(12) United States Patent
Schultz

(10) Patent No.: US 8,620,680 B2
(45) Date of Patent: Dec. 31, 2013

(54) METHODS AND APPARATUS FOR PLANNING AND MANAGEMENT OF CLINICAL TRIALS

(75) Inventor: Joshua Schultz, Waltham, MA (US)

(73) Assignee: PAREXEL International Corporation, Waltham, MA (US)

( * ) Notice: Subject to any disclaimer, the term of this patent is extended or adjusted under 35 U.S.C. 154(b) by 799 days.

(21) Appl. No.: 12/431,591

(22) Filed: Apr. 28, 2009

(65) Prior Publication Data

US 2009/0292554 A1  Nov. 26, 2009

Related U.S. Application Data

(60) Provisional application No. 61/125,693, filed on Apr. 28, 2008.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2
See application file for complete search history.

(56) References Cited

U.S. PATENT DOCUMENTS

2006/0282244 A1*  12/2006  Chotai et al. .................... 703/11
2007/0067189 A1*   3/2007  Boris et al. ........................ 705/3

OTHER PUBLICATIONS

U.S. Appl. No. 12/431,612, filed Apr. 28, 2009, Joshua Schultz.

* cited by examiner

*Primary Examiner* — Hiep V Nguyen
(74) *Attorney, Agent, or Firm* — Wolf, Greenfield & Sacks, P.C.

(57) ABSTRACT

A tool for planning and management of clinical trials. The tool computes a patient enrollment timeline in a clinical trial using multiple factors that bear on the rate of patient enrollment. The factors may be site-dependent factors or may be country-dependent factors. When these factors are applied, different sites may have different rates of enrollment in the same interval. Further, the factors may be time dependent such that even the same sites may have different enrollment rates in different intervals. Once the timeline is created, the tool may use it to calculate a schedule of monitor visits, project trial completion or otherwise generate output used in management of the clinical trial.

28 Claims, 16 Drawing Sheets

FIG. 3

Country / Timeline Information | Default Enrollment | Activation Delay

| Country | % Simple Sites | Nbr Of Sites | Country Activity Start | Std. (weeks) | Adjust (days) | Start | Weeks | Stop | Patient Type | Site Enroll Rate | Mth 1 | Mth 2 | Mth 3 | Mth 4 | Mth 5 | Mth 6 | First Mth Reduction |
|---|---|---|---|---|---|---|---|---|---|---|---|---|---|---|---|---|---|
| Australia | 50% | 1 | 1-Feb-2007 | 19.5 | -16.00 | 1-Jun-2007 | 47.71 | 30-Apr-2008 | screened | 0.71 | 1.0 | 0.0 | 0.0 | 0.0 | 0.0 | 0.0 | 50% |
|  |  |  |  |  |  |  |  |  | enrolled | 0.50 |  |  |  |  |  |  |  |
| Spain | 50% | 6 | 1-Feb-2007 | 27.0 | 0.00 | 9-Aug-2007 | 37.86 | 30-Apr-2008 | screened | 0.71 | 3.0 | 2.0 | 1.0 | 0.0 | 0.0 | 0.0 | 50% |
|  |  |  |  |  |  |  |  |  | enrolled | 0.60 |  |  |  |  |  |  |  |
| Poland | 50% | 6 | 1-Feb-2007 | 22.0 | 0.00 | 5-Jul-2007 | 42.86 | 30-Apr-2008 | screened | 0.70 | 4.0 | 2.0 | 0.0 | 0.0 | 0.0 | 0.0 | 50% |
|  |  |  |  |  |  |  |  |  | enrolled | 0.61 |  |  |  |  |  |  |  |
| Germany | 50% | 6 | 1-Feb-2007 | 20.0 | 0.00 | 21-Jun-2007 | 44.86 | 30-Apr-2008 | screened | 0.70 | 2.0 | 2.0 | 1.0 | 1.0 | 0.0 | 0.0 | 50% |
|  |  |  |  |  |  |  |  |  | enrolled | 0.61 |  |  |  |  |  |  |  |
| United Kingdom | 100% | 25 | 1-Feb-2007 | 26.0 | 0.00 | 2-Aug-2007 | 38.86 | 30-Apr-2008 | screened | 0.71 | 15.0 | 10.0 | 0.0 | 0.0 | 0.0 | 0.0 | 50% |
|  |  |  |  |  |  |  |  |  | enrolled | 0.61 |  |  |  |  |  |  |  |
| Sweden | 50% | 5 | 1-Feb-2007 | 28.0 | -30.00 | 17-Jul-2007 | 41.14 | 30-Apr-2008 | screened | 0.71 | 3.0 | 1.0 | 1.0 | 0.0 | 0.0 | 0.0 | 50% |
|  |  |  |  |  |  |  |  |  | enrolled | 0.61 |  |  |  |  |  |  |  |
| Finland | 0% | 25 | 1-Feb-2007 | 25.7 | 0.00 | 31-Jul-2007 | 39.14 | 30-Apr-2008 | screened | 0.71 | 10.0 | 10.0 | 5.0 | 0.0 | 0.0 | 0.0 | 50% |
|  |  |  |  |  |  |  |  |  | enrolled | 0.61 |  |  |  |  |  |  |  |
| United States | 100% | 30 | 1-Feb-2007 | 10.0 | 5.00 | 17-Apr-2007 | 54.14 | 30-Apr-2008 | screened | 0.70 | 12.0 | 18.0 | 0.0 | 0.0 | 0.0 | 0.0 | 50% |
|  |  |  |  |  |  |  |  |  | enrolled | 0.50 |  |  |  |  |  |  |  |
| Canada | 50% | 5 | 1-Feb-2007 | 17.3 | 0.00 | 2-Jun-2007 | 47.57 | 30-Apr-2008 | screened | 0.70 | 1.0 | 2.0 | 1.0 | 1.0 | 1.0 | 0.0 | 50% |
|  |  |  |  |  |  |  |  |  | enrolled | 0.60 |  |  |  |  |  |  |  |
| Site Total | | 109 | | | | | | | | | 51.0 | 47.0 | 9.0 | 1.0 | 1.0 | 0.0 | Study Total |
| Country Total | | 9 | | | Duration Total | 17-Apr-2007 | 54.14 | 30-Apr-2008 | | | | | | | | | Study Total |

Goal Sites

| | Nbr. | Site Var. |
|---|---|---|
| Total | 99 | 10 |

Goal Patients

| | Nbr. | Patient Var. |
|---|---|---|
| Screened | 500 | 73 |
| Enrolled | 300 | 31 |
| Completed | 100 | |
| Initiate To Screen Days | 45 | |
| Screen To Enroll Days | 60 | |

Goal Timeline

| | |
|---|---|
| Initiation Start | 1-Feb-2007 |
| Enrollment End | 30-Apr-2008 |
| Treatment End | 31-Jul-2009 |

| Country | Patient Type | Adjust Apr-07 | Adjust May-07 | Adjust Jun-07 | Adjust Jul-07 | Adjust Aug-07 | Adjust Sep-07 | Adjust Oct-07 | Adjust Nov-07 | Adjust Dec-07 | Adjust Jan-08 | Adjust Feb-08 |
|---|---|---|---|---|---|---|---|---|---|---|---|---|
| Australia | screened | 100.0% | 100.0% | 100.0% | 100.0% | 100.0% | 100.0% | 100.0% | 100.0% | 50.0% | 20.0% | 20.0% |
| | enrolled | 100.0% | 100.0% | 100.0% | 100.0% | 100.0% | 100.0% | 100.0% | 100.0% | 50.0% | 20.0% | 20.0% |
| Spain | screened | 80.0% | 100.0% | 100.0% | 100.0% | 20.0% | 70.0% | 100.0% | 100.0% | 50.0% | 80.0% | 20.0% |
| | enrolled | 80.0% | 100.0% | 100.0% | 100.0% | 20.0% | 70.0% | 100.0% | 100.0% | 50.0% | 80.0% | 20.0% |
| Poland | screened | 85.0% | 100.0% | 100.0% | 100.0% | 20.0% | 80.0% | 100.0% | 100.0% | 50.0% | 90.0% | 20.0% |
| | enrolled | 85.0% | 100.0% | 100.0% | 100.0% | 20.0% | 80.0% | 100.0% | 100.0% | 50.0% | 90.0% | 20.0% |
| Germany | screened | 100.0% | 100.0% | 100.0% | 100.0% | 20.0% | 90.0% | 100.0% | 100.0% | 70.0% | 90.0% | 20.0% |
| | enrolled | 100.0% | 100.0% | 100.0% | 100.0% | 20.0% | 90.0% | 100.0% | 100.0% | 70.0% | 90.0% | 20.0% |
| United Kingdom | screened | 100.0% | 100.0% | 100.0% | 100.0% | 20.0% | 100.0% | 100.0% | 100.0% | 50.0% | 50.0% | 20.0% |
| | enrolled | 100.0% | 100.0% | 100.0% | 100.0% | 20.0% | 100.0% | 100.0% | 100.0% | 50.0% | 50.0% | 20.0% |
| Sweden | screened | 200.0% | 200.0% | 200.0% | 100.0% | 20.0% | 100.0% | 100.0% | 100.0% | 60.0% | 60.0% | 20.0% |
| | enrolled | 200.0% | 200.0% | 100.0% | 100.0% | 20.0% | 100.0% | 100.0% | 100.0% | 60.0% | 60.0% | 20.0% |
| Finland | screened | 90.0% | 90.0% | 100.0% | 100.0% | 20.0% | 100.0% | 100.0% | 100.0% | 50.0% | 100.0% | 20.0% |
| | enrolled | 90.0% | 90.0% | 100.0% | 100.0% | 20.0% | 100.0% | 100.0% | 75.0% | 50.0% | 100.0% | 20.0% |
| United States | screened | 100.0% | 100.0% | 100.0% | 100.0% | 100.0% | 100.0% | 100.0% | 75.0% | 50.0% | 80.0% | 20.0% |
| | enrolled | 100.0% | 100.0% | 100.0% | 100.0% | 100.0% | 100.0% | 100.0% | 100.0% | 50.0% | 80.0% | 20.0% |
| Canada | screened | 100.0% | 100.0% | 100.0% | 100.0% | 100.0% | 100.0% | 100.0% | 100.0% | 50.0% | 80.0% | 20.0% |
| | enrolled | 100.0% | 100.0% | 100.0% | 100.0% | 100.0% | 100.0% | 100.0% | 100.0% | 50.0% | 80.0% | 20.0% |

FIG. 4

| Country | Status | Site No. | Site Name | CRA | Data Source | | Total Patients | Avg. Rate | Jul-07 | Aug-07 | Sep-07 | Oct-07 | Nov-07 | Dec-07 |
|---|---|---|---|---|---|---|---|---|---|---|---|---|---|---|
| Australia | Yellow | 101 | Dr. Schultz | JS | NONE | screened-expected | 7 | 0.88 | 2.0 | 1.4 | 0.7 | 0.7 | 0.7 | 0.4 |
| | | | | | | screened-actual | 9 | 0.90 | 1 | 2 | 2 | 2 | 1 | 1 |
| | | | | | | enrolled-expected | 8 | 0.95 | 0.5 | 2.0 | 1.0 | 1.0 | 1.0 | 0.5 |
| | | | | | | enrolled-actual | 7 | 0.88 | 0 | 2 | 2 | 2 | 0 | 0 |
| Spain | Green | 102 | Dr. Jones | AF | NONE | screened-expected | 3 | 0.45 | | | 0.0 | 0.5 | 0.7 | 0.4 |
| | | | | | | screened-actual | 10 | 1.67 | | | 1 | 2 | 1 | 2 |
| | | | | | | enrolled-expected | 2 | 0.38 | | | 0.0 | 0.4 | 0.5 | 0.3 |
| | | | | | | enrolled-actual | 3 | 0.50 | | | 0 | 2 | 0 | 0 |

| Monitoring Information | |
|---|---|
| CRF (min. per page) | 5.32 |
| QOL & Diary (min. per page) | 1.50 |
| Average Min. Per Page | 5.32 |
| Additional Time On Site (hrs) | 1.50 |
| Total Time On Site (hrs) | 4.35 |
| Visit Threshold Allowance (%) | 10% |
| Visit Threshold Allowance (hrs) | 0.43 |
| Monitoring Frequency (wks) | 4.00 |
| Monitoring Method | Hybrid Schedule |
| Data Management System | EDC - Inform |
| CRF Type | Web |
| Budgeted Data Collection Values | |
| Budgeted CRF | Nbr. Per Pt. | Total |
| Screen Pack | 0 | |
| Completed | 100 | 29,000 |
| Budgeted QOL & Diary | | |
| Screen Pack | 0 | |
| Completed | 36 | 10,440 |
| Budgeted CRA Monitoring Visits | | 994 |

*FIG. 12*

| Country | Site No. | Site Name | CRA | | Total | Apr-07 | May-07 | Jun-07 | Jul-07 | Aug-07 | Sep-07 | Oct-07 | Nov-07 | Dec-07 |
|---|---|---|---|---|---|---|---|---|---|---|---|---|---|---|
| Australia | 101 | Dr. Schultz | JS | CRFs - Expected | 826 | 0 | 0 | 0 | 0 | 20 | 20 | 20 | 0 | 10 |
| | | | | QOL & Diary - Expected | 0 | 0 | 0 | 0 | 0 | 0 | 0 | 0 | 0 | 0 |
| | | | | Visits - Expected | 33 | 0 | 0 | 0 | 0 | 1 | 1 | 1 | 1 | 1 |
| | | | | Visits - Actual | 0 | | | | | | | | | |
| | | | | Collected - Expected/Actual | 826 | 0 | 0 | 0 | 0 | 20 | 20 | 20 | 0 | 10 |
| Spain | 102 | Dr. Jones | AF | CRFs - Expected | 354 | 0 | 0 | 0 | 0 | 0 | 0 | 20 | 0 | 0 |
| | | | | QOL & Diary - Expected | 0 | 0 | 0 | 0 | 0 | 0 | 0 | 0 | 0 | 0 |
| | | | | Visits - Expected | 28 | 0 | 0 | 0 | 0 | 0 | 0 | 1 | 1 | 1 |
| | | | | Visits - Actual | 0 | | | | | | | | | |
| | | | | Collected - Expected/Actual | 354 | 0 | 0 | 0 | 0 | 0 | 0 | 20 | 0 | 0 |

FIG. 13

| Patient Document Completion Schedule | | | | | | |
|---|---|---|---|---|---|---|
| Treatment Month | | 1 | 2 | 3 | 4 | 5 | 6 |
| Patient Retention % | | 100.0% | 100.0% | 50.0% | 100.0% | 75.0% | 100.0% |
| | | Enter nbr. of pages per patient per month during treatment | | | | | |
| CRF | Screen Pack | 0 | | | | | |
| | Completed | 10 | 5 | 5 | 5 | 5 | 20 |
| QOL & Diary | Screen Pack | 0 | | | | | |
| | Completed | 0 | 0 | 0 | 0 | 0 | 0 |
| Number of CRF pages with Retention | | 10 | 5 | 2.5 | 5 | 3.75 | 20 |
| Number of QOL/Diary pages with Retention | | 0 | 0 | 0 | 0 | 0 | 0 |

FIG. 14

| Country | | Total | Apr-07 | May-07 | Jun-07 | Jul-07 | Aug-07 | Sep-07 | Oct-07 | Nov-07 | Dec-07 |
|---|---|---|---|---|---|---|---|---|---|---|---|
| Australia | CRFs - Expected | 826 | 0 | 0 | 0 | 0 | 20 | 20 | 20 | 0 | 10 |
| | QOL & Diary - Expected | 0 | 0 | 0 | 0 | 0 | 0 | 0 | 0 | 0 | 0 |
| | Visits - Expected | 33 | 0 | 0 | 0 | 0 | 1 | 1 | 1 | 1 | 1 |
| | Visits - Actual | 0 | 0 | 0 | 0 | 0 | 0 | 0 | 0 | 0 | 0 |
| | Collected - Expected/Actual | 826 | 0 | 0 | 0 | 0 | 20 | 20 | 20 | 0 | 10 |
| Spain | CRFs - Expected | 1,802 | 0 | 0 | 0 | 0 | 0 | 10 | 54 | 35 | 23 |
| | QOL & Diary - Expected | 0 | 0 | 0 | 0 | 0 | 0 | 0 | 0 | 0 | 0 |
| | Visits - Expected | 140 | 0 | 0 | 0 | 0 | 0 | 2 | 4 | 4 | 5 |
| | Visits - Actual | 0 | 0 | 0 | 0 | 0 | 0 | 0 | 0 | 0 | 0 |
| | Collected - Expected/Actual | 1,802 | 0 | 0 | 0 | 0 | 0 | 10 | 54 | 35 | 23 |

METHODS AND APPARATUS FOR PLANNING AND MANAGEMENT OF CLINICAL TRIALS

RELATED APPLICATIONS

This application claims priority under 35 U.S.C. §119(e) to U.S. Provisional Application Ser. No. 61/125,693, entitled "METHODS AND APPARATUS FOR PLANNING AND MANAGEMENT OF CLINICAL TRIALS," filed on Apr. 28, 2008, which is herein incorporated by reference in its entirety.

TECHNICAL FIELD

The present disclosure is directed generally to methods and apparatus for planning and managing clinical trials, some aspects for which include methods and apparatus for planning and managing patient recruitment for clinical trials.

BACKGROUND

Obtaining approval for a therapeutic product (e.g., a medical device, a pharmaceutical product such as a drug, etc.) requires a clinical trial in which the therapeutic product is tested on human subjects to validate the product's safety and efficacy for its intended purpose. To ensure that the results of the clinical trials are reliable and that results are reproducible, many clinical trials are often multi-site and/or multinational operations which typically require substantial planning and oversight to run efficiently. For example, a clinical trial may involve hundreds or thousands of patients recruited worldwide, and a central management service may be employed to manage various aspects of the clinical trial.

When planning a clinical trial, it is often desirable to estimate the amount of time necessary to recruit and enroll a predetermined number of patients on which the therapeutic product will be tested. The developer/manufacturer of the therapeutic product has a substantial economic interest in obtaining approval as quickly as possible to expedite return on their investment, thus often rendering accurate prediction of the clinical trial timelines essential. Conventional methods of estimating patient recruitment timelines for clinical trials typically consider only the number of sites and the desired number of patients to be recruited. A straight line extrapolation is then typically performed based on the number of patients expected to be recruited on a per site per month basis. However, such linear estimation models lead to inaccurate predictions of the number of patients that can be recruited in a given amount of time, and ultimately, underestimate the time it will take for a clinical trial to complete. By the time the problem is recognized, it may be too late to add sites or otherwise correct the problem. Thus, clinical trials planned using conventional methods may be at risk for taking longer to complete than predicted, often by substantial amounts.

SUMMARY

In one aspect, the invention relates to a tool for clinical trial management. The tool includes factors affecting patient enrollment rates during a clinical trial. The factors define non-uniform rates of patient enrollment at a plurality of clinical trial sites in different time intervals of a plurality of time intervals. The factors also define different rates of patient enrollment in different clinical trial sites during the same time interval of the plurality of time intervals. Computer executable instructions use the factors to compute a patient enrollment timeline for the clinical trial. The computing involves projecting a number of patients enrolled at the plurality of sites during each of the plurality of time intervals, and providing as an output, the patient enrollment time line.

In another aspect, the invention relates to an apparatus that computes, for each of a plurality of time intervals, a projection of a number of patients enrolled in a clinical trial. The computing involves obtaining data identifying a plurality of clinical trial sites and obtaining data defining non-linear patient enrollment rates at the plurality of clinical trial sites. Using the data defining non-linear patient enrollment rates, a number of patients enrolled for each of the plurality of sites during each of the plurality of time intervals is computed.

In yet a further aspect, the invention relates to a method of operating a computer to produce an enrollment timeline for a clinical trial. The method includes obtaining data identifying a plurality of clinical trial sites. This data includes, for each clinical trial site, a country in which the clinical trial site is located. Data defining a plurality of factors relating to patient enrollment rates at the plurality of clinical trial sites is also obtained. These factors include a country-dependent factor and a site-dependent factor. Using the plurality of factors, a projection of a number of patients enrolled for each of the plurality of sites during each of a plurality of time intervals is computed, and a projection of a number of patients enrolled in a clinical trial for each of a plurality of time intervals is provided as an output.

The foregoing is a non-limiting summary of the invention, which is defined solely by the appended claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3 is a sketch of a user interface for a computer implemented tool for planning and management of clinical trials;

FIG. 4 is a sketch of a user interface through which a user may enter month-to-month adjustments, thereby defining non-linear patient enrollment rates;

FIG. 8 is a sketch of a graphical user interface for a tool for clinical trial planning and management showing status of individual trial sites;

FIG. 12 is a sketch of a monitoring information that may be used by a tool for clinical trial planning and management;

FIG. 13 is a sketch of a user interface through which a tool for clinical trial planning and management may present a schedule for monitoring visits at sites participating in a clinical trial;

FIG. 14 is a sketch of a user interface for a tool for clinical trial planning and management that incorporates patient retention into a model for computing a monitoring schedule;

FIG. 15 is a sketch of a user interface for a tool for clinical trial planning and management that projects monitoring visits at trial locations.

DETAILED DESCRIPTION

Figure 1:
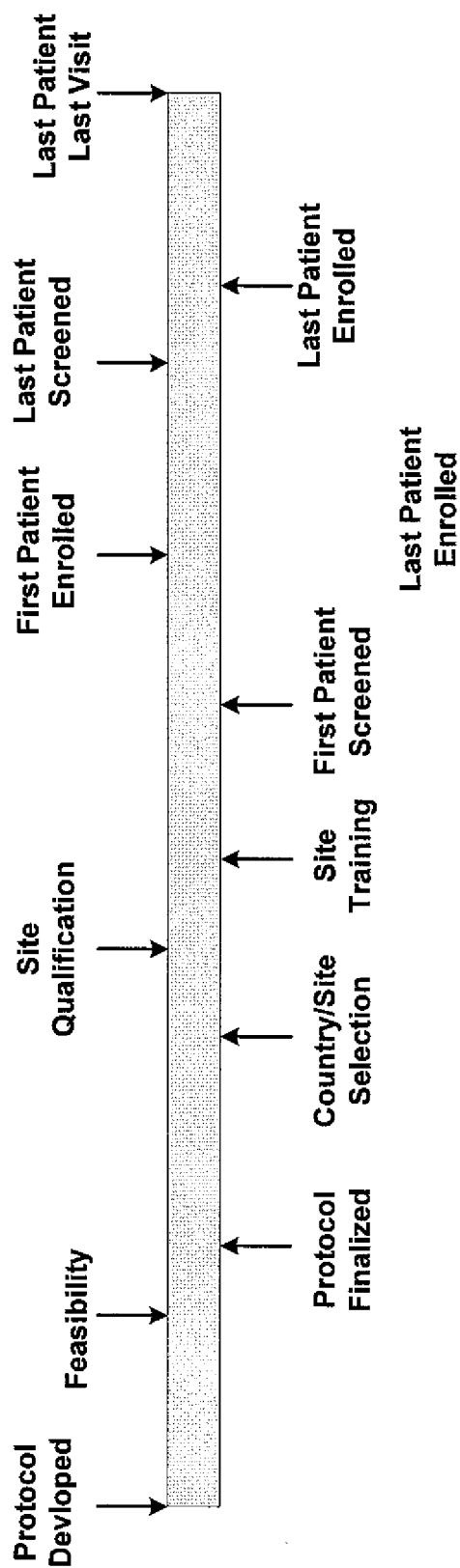
FIG. 1 is a sketch of a generic timeline for a clinical study.

As discussed above, conventional methods for clinical trial forecasting and planning are crude and often inaccurate and unreliable. In particular, conventional straight line extrapolation models for estimating patient recruitment frequently underestimate the time necessary for completing the clinical trial, thus costing the sponsor of the clinical trial time and money and delaying their return on investment (ROI).

Applicant has recognized and appreciated that previous methods of patient recruitment planning for clinical trials may not be adequate in providing an accurate timeline for completing the clinical trial due, in part, to a reliance on assumptions that the overall rate of recruitment is substantially constant throughout the life of the clinical trial. In addition, conventional recruitment planning may also operate on the assumption that various clinical trial sites recruit patients at substantially the same or similar rates and/or will start-up at substantially the same time. Applicant has appreciated that these assumptions are generally incorrect. Thus, some embodiments of the present invention are directed to methods and apparatus for providing a patient recruitment timeline based on one or more factors that tend to drive patient recruitment at a different rate than conventionally assumed (e.g., at a different rate then conventionally assumed by conventional linear modeling techniques).

Applicant has recognized and appreciated that more accurate patient recruitment timelines may be provided from the outset of a clinical trial if one or more factors affecting patient recruitment are included in the development of the timelines. In view of the foregoing, some embodiments of the present invention are directed to methods and apparatus for determining a patient recruitment timeline for a clinical trial by incorporating at least some of these factors.

According to some embodiments, methods and apparatus for planning patient recruitment for a clinical trial by generating a timeline based on at least one country-dependent factor and at least one site-dependent factor are provided. The at least one country-dependent factor and the at least one site-dependent factor may be determined from observed historical trends in patient recruitment, or from information obtained from sites and/or countries participating in a clinical trial. Any one or combination of factors (e.g., country-dependent/site-dependent factors) may be used to generate the timeline, as described in further detail below.

Applicant has also recognized that ongoing monitoring and assessment of patient recruitment during a clinical trial may provide valuable information for reducing the duration of the clinical trial and/or ensuring that the clinical trial is proceeding substantially as expected. Thus, some embodiments of the present invention are directed to methods and apparatus for providing an adaptive framework for patient recruitment management during a clinical trial. The framework facilitates tracking the recruitment progress of individual sites to identify sites which are not meeting recruitment expectations, thereby enabling strategic decisions to be made in real-time to mitigate or remedy departures from the predicted timeline for the clinical trial.

Applicant has further appreciated that management of clinical research assistants (CRA) and other human resources may often present a significant bottleneck in performing and completing a clinical trial. For example, CRAs may be a relatively costly and limited resource and therefore the effective use of CRAs, such as intelligently scheduling monitoring visits and the timely collection of data from the various sites in the clinical trial, may be an important factor in managing a clinical trial and streamlining the process to ensure that projected timelines are substantially met. Thus, some embodiments of the present invention are directed to methods and apparatus for scheduling monitoring visits based at least in part on information about the individual sites in the clinical trial. For example, the amount of data to be collected at each of the sites, and/or minimum or maximum durations between visits may be used as guidelines to efficiently schedule CRA visits.

As discussed above, successful completion of a clinical trial may be an important step towards the approval of a drug, medical device or other therapeutic product since the results of the clinical trial may provide the necessary regulatory indication that the product is safe and effective for its intended use. However, the time it takes to complete a clinical trial varies widely from trial to trial and may depend on various factors including the number and type of selected clinical trial sites, the target patient population to be recruited for the trial, and other factors such as historical information about patient recruitment for particular sites or countries. Despite some development of improved recruitment practices, patient recruitment remains a major factor in determining the length of clinical trials.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In particular, numerous methods are described in the context of an exemplary software tool. However, any one or combination of the methods and apparatus described herein may be used, as the aspects of the invention are not limited in this respect. In addition, although various methods are described in connection with a software tool embodiment, in some embodiments, the various methods may be incorporated into a plurality of separate software tools in any desired combination, as the aspects of the invention are limited for use with any particular software implementation.

FIG. 1 illustrates an example of a typical progression or generic timeline for a clinical study, from protocol development until the last patient has completed his or her last visit. As discussed above, clinical trials are often multi-national trials wherein each country has a predetermined number of sites that are simultaneously performing the trial (e.g., recruiting, screening, enrolling and testing the target therapeutic product on the enrolled patients). Conventional methods of projecting how long a clinical trial will take typically assume that all sites in all countries are performing the clinical trial at the same rate. That is, conventional methods often assume that all sites are initiated at the same time and that patient recruitment is achieved at a relatively constant per patient per site rate. However, this assumption leads to inaccurate projections of when the clinical trial will be completed.

Applicant has appreciated that the each country and each site may have a different timeline signature from the time of site qualification to the time the last patient completes his/her last visit. That is, not only does start-up and recruitment duration vary from site to site and country to country, but so does the timing at which the various sites in the selected countries meet the various benchmarks indicated on the generic time-line in FIG. 1 (e.g., first patient screened, first patient enrolled, last patient screened, last patient enrolled, last patient's last visit, etc.).

Accordingly, using conventional projection methods, a sponsor of a clinical trial, at the time of the country/site selection stage, would generally assume a linear model based on the number of sites and the projected number of patients per month at each site to predict when the last patient would complete his/her last visit. However, as discussed above, this linear model ignores the rich amount of variability in the timelines amongst the sites located in the various countries selected for the clinical trial, resulting in inaccurate projections which may cost the sponsor substantial time and money.

Figure 2:
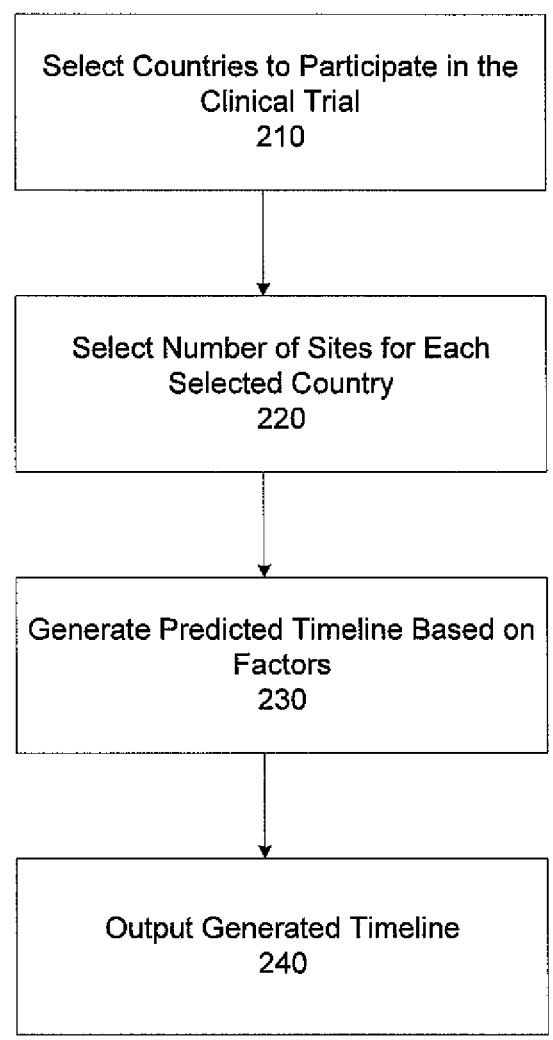
FIG. 2 is a flowchart of a method of estimating a patient recruitment timeline for a clinical trial.

FIG. 2 illustrates a method of estimating a patient recruitment timeline for a clinical trial for a therapeutic product by modeling at least some of the variability between sites and countries involved in the clinical trial, in accordance with some embodiments of the present invention. In act 210, a plurality of countries is selected for participating in a clinical trial. The number of countries selected may depend on the type of the therapeutic product, the size of the clinical trial, the projected budget for the clinical trial, and/or a projected length of the clinical trial. Which countries are selected may also depend on one or more of the above factors. In act 220, a number of sites for each country is selected to begin patient recruitment planning for the clinical trial.

In act 230, a patient recruitment timeline is generated based, at least in part, on at least one country dependent factor and at least one site dependent factor. A country dependent factor includes any factor that impacts patient recruitment and exists as a function of the particular country for which the factor is applied. Country dependent factors include, but are not limited to, delays associated with country specific regulations that may either accelerate or delay sites in a particular country from starting patient recruitment, holidays or vacation trends associated with the country, availability of clinical research assistants (CRAs) in a given country, etc. Site dependent factors include any factor that impacts patient recruitment and exist as a function of the particular site, or type of site for which the factor impacts. Site dependent factors may include, but are not limited to, the complexity of the site (e.g., a private practice or a hospital), whether the site has an existing patient database, site fatigue, etc., which factors and others are described in further detail below.

In act 240, the generated timeline is displayed for viewing to, for example, determine if the timeline is consistent with the goals of the clinical study. For example, the timeline may be plotted, or may have a numerical representation that indicates to a user when the clinical trial is estimated to be completed. Because all sites are not treated the same, and the assumption that sites recruit the same number of patients per month throughout the trial is not relied upon, the resulting timeline may be more predictive of the actual completion of the clinical trial. That is, because at least some country dependent and/or site dependent factors were used to model the clinical trial instead of the simple model of projecting a timeline based on a linear extrapolation using the number of patients recruited per month per site, the timeline may be more accurate in predicting when the clinical trial will be completed.

Applicant has developed a tool, which may be implemented as one or more software programs, to assist in patient recruitment that incorporates or models a number of factors appreciated by the Applicant as impacting the patient recruitment process. FIG. 3 illustrates a screen shot of a portion of the software tool that may be used to estimate a patient recruitment timeline for a clinical trial, in accordance with some embodiments of the present invention. The software tool may include an information table 300 wherein information may be entered that may be useful in planning a clinical trial, for example, information that may facilitate accurately predicting a timeline for a given clinical trial. For example, information table 300 may be populated, at least in part, during the country/site selection phase illustrated in the generic timeline illustrated in FIG. 1.

The information table 300 may comprise entries for a list of countries 310 in which the clinical trial will take place, and various factors which affect the recruitment timeline in each of the respective countries. The list of countries may be selected in number and geography to suit a particular clinical trial. Applicant has appreciated that many factors may play a role in how long a clinical trial will take to complete, some of which may be country specific, some of which may relate to the type of site, and some of which may relate to the type of investigator, as discussed in further detail below. An estimated patient recruitment timeline may include any number and/or type of such factors, and embodiments of the invention are not limited for use with any particular number or type of factor.

Each selected country may have a designated number of sites 312 participating in the clinical trial. As with the choice of countries, the number of sites within each country may be selected to best suit the needs of the clinical trial being planned. For example, in FIG. 3, Spain has six sites participating in the trial, whereas the United States has thirty sites. However, the number of countries and the number of sites in each country in FIG. 3 are exemplary and provided merely to illustrate certain aspects of the invention. As discussed above, any number of countries and/or sites may be selected and entered into information table 300. Indeed, the number and combination of countries/sites may depend on the pharmaceutical/device being tested, and/or the size of the clinical trial, etc.

As discussed above, conventional planning for clinical trials typically operate on the assumption that all sites in the clinical trial are initiated at substantially the same time. Applicant has appreciated from historical data that this assumption is incorrect, and recognized that planning a clinical trial using this incorrect assumption may significantly contribute to inaccurate timelines. Indeed, Applicant has appreciated that the type of site may significantly impact the start-up time. According to some embodiments, each site may be classified in categories indicative of how long a site, on average, is likely to take in starting up.

A relatively straightforward classification includes categorizing each site as being either simple or complex. In general, complex sites may be institutions that require a longer start-up time than simple sites, such as, for example, a relatively large university or hospital, where the regulatory processes involved with approving the clinical trial may be relatively extensive. For example, in a university, an Institutional Review Board (IRB) associated with the university must approve the university's role in the clinical trial. The IRB may meet infrequently, thereby delaying the site's effective initiation date. A simple site may be a smaller institution, such as a private practice clinic, which may have a more expedient approval process or fewer regulatory or bureaucratic obstacles to overcome before start-up or initiation.

Other factors may also be considered instead of, or in combination with, the length of the anticipated approval process to determine if a site should be classified as a simple site or a complex site. For example, site classification may be based, at least in part, on the availability of sites in a particular country, historical data indicating the speed with which sites have typically been initiated, or any other suitable information. It should be appreciated that the bipartite classification of simple vs. complex described above is not limiting, as the classification system for categorizing sites can have any number of categories such that sites can be classified at any desired level of granularity.

To this end of classifying the sites participating in the clinical trial, information table 300 comprises entries for inputting site classification information 314, which specifies the percentage of simple sites for each country. As shown in the example of FIG. 3, 50% (3 of 6) of the sites in Spain are classified as simple, with the other 50% being classified as complex, whereas 100% (30 of 30) of the sites in the United States are classified as simple. While site classification information 314 in FIG. 3 corresponds to the percentage of simple sites, it should be appreciated that any other method of specifying the percentage of simple versus complex sites is also possible, or any other method of specifying the relative distribution of sites in each chosen classification category may be used, as the aspects of the invention are not limited in this respect.

Accordingly, when determining a number of sites beginning patient enrollment during an interval, sites of different types may be considered separately. For example, based on historical data, a percentage of simple sites beginning patient enrollment during a month may be determined. Separately, a percentage of complex sites beginning patient enrollment during that month may be determined from historical data. In computing an enrollment timeline for a clinical trial, the number of new sites enrolling patients in each of a plurality of intervals may be computed by summing the number of simple sites multiplied by the percentage of simple sites expected to begin enrolling patients with the number of complex sites multiplied by the percentage of complex sites expected to begin enrolling patients.

Applicant has appreciated that not all sites in a country will begin recruiting patients in the first month of the clinical trial due to variations in the number and type of sites in each country. As discussed above, complex sites may take longer to initiate than simple sites due to delays in protocol approval, regulatory procedures, etc. Thus, in some embodiments, an estimate of the number of sites expected to be activated in each month of the clinical trial may be calculated and/or entered as site activation delay 316. The site activation delay indicates, for each country selected for the clinical trial, how many sites are projected to be initiated each month during the clinical trial. The site classification information, coupled with the number of sites in each country may be used to estimate the site activation delay.

Additional information may also be combined with the number and type of sites to derive site activation information 316. For example, site activation delay 316 may be weighted so as to favor the activation of simple sites in the early months. Thus, if a country (e.g., United States) has a higher percentage of simple sites than another country (e.g., Spain), the country with a higher percentage of simple sites will typically activate sites at a faster rate, and will tend to begin screening/enrolling patients at a rate accelerated from countries with a large percentage of complex sites. For example, even though the U.S. has the most sites to initiate, because all of the sites are classified as simple, the U.S. is still projected to initiate all of the sites in the first two months.

As discussed above, site activation may require a number of processes to be performed before the site can be activated. For example, it is typically required that a research protocol be finalized and approved by an oversight committee to weigh the risks and benefits of the clinical trial and to ensure that the trial will be conducted safely. In some embodiments, the date at which the finalized protocol is typically available in each country may be entered as activation start information 318. The activation start date may be the same for each country (as in FIG. 3) due, in part, because once the protocol has been finalized, it can be distributed at substantially the same time to all sites. However, in some cases, different countries may include different or additional approval processes and the activation start date may be different for certain countries to account for these differences (e.g., to account for differing dates when sites in the country receive and/or approve the final protocol).

The different regulatory and site initiation procedures in different countries may vary considerably, perhaps leading to a wide range of delays amongst the selected countries before the clinical trial may be approved and patient screening and enrollment may begin. For example, before a site can be initiated it may have to go through processes including, but not limited to, completing a site regulatory package, receiving and completing a participation contract, EC/IRB submission and approval, regulatory submission and approval, license import, approval of the regulatory package and the initiation visit. These processes may vary in duration and complexity from country to country. In addition, some of these regulatory processes may be absent in some countries, and some countries may have additional processes.

To model these factors into a clinical trial timeline, a standard initiation time may be entered into the tool as initiation start information 320. The standard initiation time for each country may be derived from historical data, although standard initiation times may be determined using any other suitable means including, but not limited to, information provided by at least some of the sites or countries, or other information, such as that provided by regulatory bodies such as the Food and Drug Administration (FDA) or the European Medicines Agency (EMEA).

In FIG. 3, the standard initiation times are specified in weeks. That is, the initiation start information 320 indicates the number of weeks it takes, on average, for the associated country to complete all the initial regulatory and activation processes to the time the site actually begins recruiting patients. The delay can be measured in days, weeks, months, or any other time increment, as aspects of the invention are not limited in this respect. By modeling some of the regulatory factors in the various countries, a more accurate timeline may be generated, and in particular, a more accurate start date (e.g., the site initiation date, or the date the first patient is screened) for each country may be estimated.

Other circumstances may also cause delays in patient recruitment in addition to the standard initiation times. For example, if the clinical trial involves a pharmaceutical product, shipping times of the pharmaceutical product to various countries may be delayed and/or accelerated based on certain factors, such as drug shipping regulations, customs delays, etc. Accordingly, an adjustment time may be entered as adjustment information 322 for each country to account for further variability between countries. In FIG. 3, the adjustment times are specified in days. However, such adjustments may be made using any desired increment of time. It should be appreciated that the adjustment information may be used for other factors that result in variability in recruitment, as the aspects of the invention are not limited in this respect.

In some embodiments, a desired completion date for the clinical trial may also be entered as completion information 324. In general, the completion date may be the same for each country, as shown in FIG. 3. However, in some circumstances, the completion date may differ between countries, and this difference may be accounted for when entering completion information 324.

By using at least some of the aforementioned factors and the associated information, enrollment information 330 may be calculated. The enrollment information may include any information related to the duration of the enrollment period for each country participating in the clinical trial. For example, in some embodiments, a start date 332 may be calculated based, at least in part, on activation start information 318, initiation start information 320, and adjustment information 322. That is, various site-dependent and country dependent information may be used to obtain a more accurate start date for each country, resulting in a timeline that may more accurately reflect the actual clinical trial. However, any one or combination of factors may be used to determine a start date for the enrollment period for the associated countries, as the aspects of the invention are not limited in this respect.

Additionally, enrollment duration information 334 may be calculated based on information provided in information table 300. Enrollment duration information 334 describes the interval of time during which patient enrollment may take place at sites in each country. In some clinical trials, a common enrollment completion date may be determined for all sites in the clinical trial, and enrollment duration information 334 may provide a quickly ascertainable measure of the enrollment period based at least in part on the difference in time between the completion date 324 and start date 332. However, the completion date need not be uniform and may differ between countries, as the aspects of the invention are not limited in this respect.

Patient recruitment for many clinical trials proceeds in at least two stages; screening and enrollment, which may overlap in time as illustrated in the generic timeline illustrated in FIG. 1. During the screening stage, patients are evaluated to determine if they meet the entrance criteria to be enrolled in the clinical trial. For example, a medical history may be taken, including, for example, current and previous medication use, history of smoking or alcohol use, family medical histories, etc. During the screening period, some preliminary tests, such as blood and/or urine tests, blood pressure measurements, ECG measurements, etc. may also be administered to help determine a patient's eligibility to participate in the clinical trial. Additionally, some clinical trials may require patients to be free from particular medications for a pre-specified length of time before enrolling in the clinical trial. Thus, the screening period may also be used as a "wash-out" period during which some patients may stop taking medications that would otherwise exclude them from participating in the clinical trial.

After the screening period has commenced, and a patient has satisfied all of the entrance criteria set forth in the clinical trial's protocol, the patient may be enrolled in the clinical trial, and the enrollment period may begin. In a typical clinical trial, the enrollment period may be characterized by a series of patient visits during which the performance and/or health of the patient is evaluated by a doctor or other clinical research professionals. Various tests may be performed on or with the patient during the patient visits, and the results of the tests may be recorded on a standardized form such as a clinical research form (CRF), or any other suitable form so that the test results of all patients participating in the clinical trial may be collected and analyzed over the course of the clinical trial.

Not all patients that are screened will ultimately satisfy the entrance criteria for enrollment in a clinical trial. Therefore, the number of patients that will need to be screened is necessarily greater than the number of patients expected to be enrolled in the clinical trial. Thus, Applicant has appreciated that estimated patient recruitment timelines may be better modeled if they include information about both the screening period and the enrollment period. Accordingly, in some embodiments, information table 300 may additionally comprise space to enter initiate-to-screen information 340 and screen-to-enroll information 342.

Initiate-to-screen information 340 indicates, on average, the length of time that it takes for a site to screen their first patient after the site has been initiated (i.e., the interval of time from when the site has a final and approved clinical trial protocol to the time the first patient is screened). Screen-to-enroll information 342 indicates, on average, the length of the screening period (i.e., the time during which a patient is being screened but has not yet been enrolled in the clinical trial). For example, screen-to-enroll information 342 may incorporate information about the number of "wash-out" days required for particular medications and/or any other screening information which may affect the length of the screening period, such as the length and complexity of the tests that must be performed, the number of required patient visits, etc.

Information table 300 may further comprise space to enter site enrollment rate information 328, indicating the number of patients expected to be screened and/or enrolled at each site during a pre-specified time period. Because site enrollment rate information 328 reflects an estimate of the number of patients that will be recruited at each site in a country during a pre-specified time period, the value of site enrollment rate information 328 may be a non-integer value. For example, if in a previous 12-month clinical trial, a country had 10 sites, and the total number of recruited patients was 84, site enrollment information may be indicated as 0.7 (i.e., 84 patients/10 sites/12 months). The site enrollment rate may be obtained from historical information, past performance of the sites, etc.

In FIG. 3, the pre-specified time period for the site enrollment rate is one month, although any other suitable time period may also be used. In Australia, it is expected that sites will screen 0.71 patients per month and enroll 0.5 patients per month over the duration of the clinical trial. In contrast, sites in Spain expect to also screen 0.71 patients per month, but expect to enroll 0.6 patients per month over the duration of the clinical trial. As discussed above, site enrollment rate information 328 may be based in part on historical data related to screening and enrollment success for various sites in a country, provided by, for example, the individual sites, clinical research management companies, or by any other source. Such enrollment information may be useful in more accurately modeling a clinical trial and generating more predictive timelines. In addition, the enrollment information may be useful in managing a clinical trial to, for example, monitor sites and identify sites that may not be performing as predicted, as discussed in further detail below.

Applicant has recognized that their exist other site and/or country dependent factors that may only effect a portion of the clinical trial, for example, a speed-up or slow-down in recruitment due to one or more of these factors. For example, seasonal variations, holidays, site-fatigue, or other non-linear factors may be included in recruitment planning to produce a more accurate patient recruitment timeline. Applicant has appreciated that incorporating one or more of these factors into the clinical trial model may facilitate more accurate timelines. FIG. 4 illustrates a screen shot of a portion of the patient recruitment tool where further information may be entered to account for additional factors that may impact recruitment rates or otherwise effect the patient recruitment in a clinical trial.

The screen shot in FIG. 4 includes an information table 400 having entries to provide various adjustments to the month-by-month patient recruitment rates based on characteristics of the respective countries, and/or respective sites. For example, it may be determined from historical data, or otherwise, that many people in Germany (and other countries in Europe) tend to be on vacation during August, and people in Australia tend to be on vacation in January. Thus, it may be the case that patient recruitment at sites in Germany may be lower than expected during August, and recruitment at sites in Australia may be lower than expected in January. Accordingly, the expected patient recruitment (screening and/or enrollment) may be adjusted by entering, for example, a reduced percentage (e.g., 20%) of predicted recruitment in recruitment adjustment percentages 410 during August and January, for Germany and Australia, respectively, to account for these seasonal variations, as shown in FIG. 4.

In addition to seasonal variations, the timing of holidays may also result in a predictable slowdown in patient recruitment for various countries. For example, sites in China may have lower patient recruitment around Chinese New Year, and many sites throughout the world may have lower recruitment during the holiday season in December. Thus, holiday information may also be reflected in recruitment adjustment percentages 410 entered in information table 400. Other country-dependent factors may also be incorporated into the recruitment estimates to create a more accurate timeline, as aspects of the invention are not limited for use with any particular factor or combination of factors.

Applicant has recognized that consideration of other site-dependent non-linear factors may also facilitate developing an accurate patient recruitment timeline for a clinical trial. Two such factors are referred to herein as the "database effect" and "site fatigue." The database effect is related to the ability of a site to rapidly recruit patients at the beginning of a clinical trial. Some sites may be well-established research centers, and consequently may have large databases of patients who have participated in previous clinical trials, and who have indicated that they are willing to participate in future clinical trials. Other types of sites may also have invested in generating and maintaining a database that lends itself to accelerated patient recruitment at the beginning of the recruitment period. Prior to site initiation, or shortly thereafter, such sites may contact potential patient recruits from the database to inform them about the clinical trial and/or the criteria for enrollment in the trial.

As such, sites with large databases may be able to recruit substantially more patients at the beginning of a clinical trial than sites lacking such databases. To account for this database effect, countries having many sites with known databases may recruit more than the expected number of patients early in the clinical trial, and this also may be indicated by adjusting recruitment adjustment percentages 410 indicated in the information table 400. For example, it may be known from historical data or otherwise that many sites in Sweden have large databases, and typically exhibit some level of the database effect. Thus, as shown in FIG. 4, Sweden, where site initiation is targeted for April, 2007, the recruitment adjustment percentages 410 for Swedish sites may be increased to a higher value (e.g., 200%) during the first three months after site initiation (e.g., April, May, June), to account for the database effect.

Another factor that may be important to model is site fatigue. For various reasons, near the end of a clinical trial, some (or all) sites may begin recruiting patients at a slower rate than expected. For example, a site may have exhausted its patient database or the viable patient population in a region may have been mined such that there may be significantly fewer patients in the area who meet the entrance criteria and/or who are willing to participate in the clinical trial. Alternatively, some sites may be conducting multiple clinical trials, and they may invest less recruiting resources into a clinical trial that is nearing completion. For these reasons and others, the recruiting rate of some sites may be diminished toward the anticipated end of a clinical trial. Thus, to account for the effect of site fatigue, the recruitment adjustment percentages 410 for some or all of the countries in which the clinical trial is to be conducted may be adjusted toward the end of the recruitment period.

As shown in FIG. 4, the last month of the exemplary clinical trial may be February, 2008. During this month, all of the sites may be experiencing site fatigue, and the patient recruitment adjustment percentages are reduced (e.g., to 20%) to reflect this. In some embodiments, historical information may be used to determine the amount and/or duration of site fatigue for various countries so that the appropriate adjustment percentages may be selected accordingly. Although, in some instances (as in FIG. 4), the degree and/or duration of site fatigue may be assumed to be uniform across all countries, information indicating specific site fatigue values for particular countries may be incorporated as well.

Other site-dependent factors may also be important in estimating a patient recruitment timeline. For example, historically, clinical research sites tend to show lower than expected patient recruitment during the first month of the clinical trial. Some sites may not recruit any patients at all during the first month, whereas other sites may recruit only half the number of expected patients during the month. Referring back to FIG. 3, to capture this first month recruitment reduction phenomenon, information table 300 may additionally comprise entries for reduction information 326, which specifies a reduction in the number of patients expected to be recruited during the first month of the clinical trial for each site and/or country participating in the clinical trial.

The reduction information 326 may be specified as a percent reduction in patients that will be enrolled during the first month, as shown in FIG. 3, or reduction information 326 may be specified in any other suitable way including, but not limited to, the actual number of expected patients to be recruited during the first month, and/or the magnitude of the reduction. In FIG. 3, the reduction information is indicated as the average percent reduction across all sites in a country, resulting in only one entry per country. However, each country could have more than one entry (e.g., an entry for each site) and the first month phenomenon may be captured at any level of granularity.

Some or all of the aforementioned information may be used to construct a patient recruitment timeline for each site and/or country, and a patient recruitment timeline for the clinical trial as a whole. In some embodiments, patient recruitment timelines may be presented in numerical form, such as recruitment table 500 shown in FIG. 5. Recruitment table 500 shows the target number of patients to be screened and enrolled in the clinical trial for each month over the duration of the clinical trial, for each selected country. Based on the information provided in information table 300, the total expected number of patients recruited is indicated for each country as patient total information 510, which has components for the total number of patients expected to be screened and enrolled, respectively. Similarly, based on information table 300, the rate (e.g., number of patients per month) at which each site in a particular country is expected to recruit patients is indicated as country enroll rate information 520, which also has components for both screening and enrolling.

Figure 5:
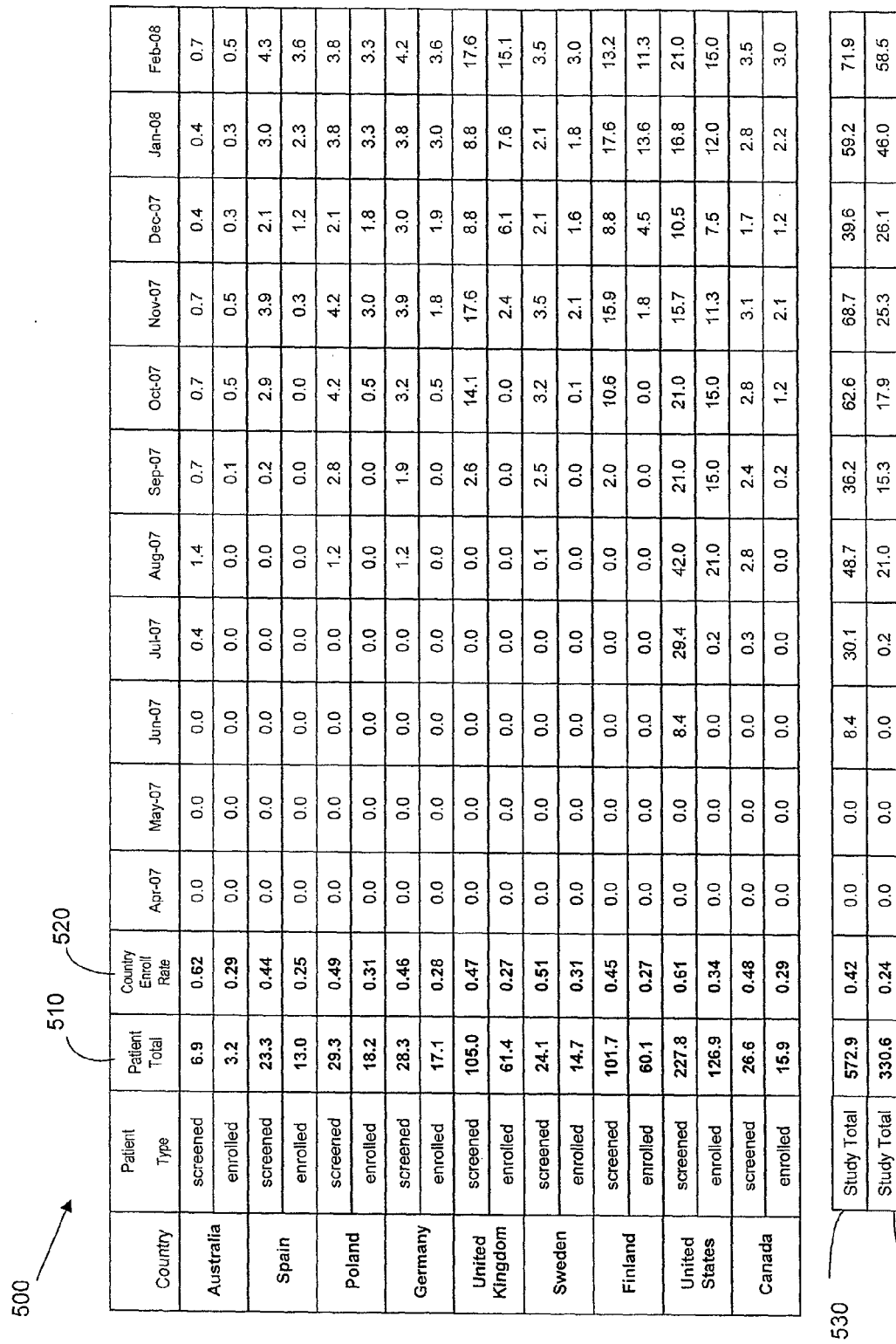
FIG. 5 is a sketch of a user interface to a tool for clinical trial planning and management illustrating a patient recruitment timeline in tabular form.

Based on patient recruitment timelines for individual countries, an overall patient recruitment timeline may be calculated for the clinical trial. For example, as shown in FIG. 5, based on data entered into the tool, the expected total number of patients to be screened in the clinical trial may be 572.9 as indicated by screened total information 530, and the expected total number of patients to be enrolled in the clinical trial may be 330.6 as indicated by enrolled total information 540, which is also broken down for each month of the clinical trial.

Figure 6:
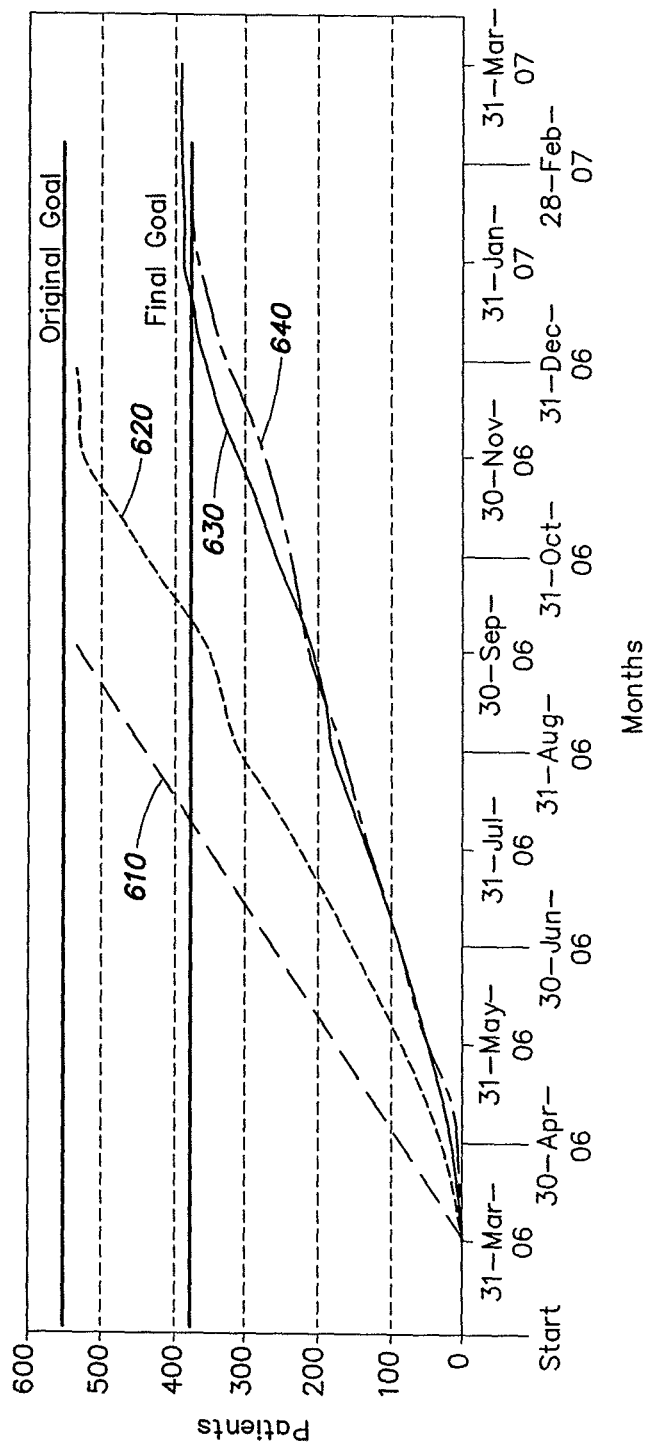
FIG. 6 is a sketch of an alternative format for displaying a patient recruitment timeline generated by a tool for a clinical trial planning and management and including projections generated in multiple ways.

The information entered into the software tool may be graphically depicted as a timeline. FIG. 6 illustrates timelines generated using conventional linear extrapolation models, timelines generated using combinations of the factors described herein, and actual recruitment data from an exemplary clinical trial. For example, timeline 610 was generated using a linear extrapolation model based on a predicted enrollment rate projected as a straight line projection of number of patients per site per month. As shown, the linear model predicts that 550 patients will be enrolled by September $30^{th}$. However, as shown by the actual patient enrollment timeline 640, this prediction is substantially off the mark. Accordingly, a sponsor relying on the linear model timeline may be unpleasantly surprised, at the expense of time and money, when the clinical trial takes substantially longer than predicted.

Timeline 620 was generated using a first combination of factors described above. In particular, timeline 620 was generated by incorporating factors that tend to cause a deviation from conventional straight-line estimation. As shown, timeline 620 is a much better predictor of actual patient recruitment than timeline 610 generated using the straight-line extrapolation technique due to the more accurate results achieved by modeling a richer set of factors that impact patient recruitment.

As discussed above, conventional straight-line techniques apply a predetermined enrollment rate (i.e., number of patients per site per month) and use this rate as the slope of the linear projection. Conventionally, the enrollment information is obtained by using predictions provided by the various sites. However, Applicant has appreciated that sites often overestimate the number of patients they are capable of enrolling, and that such unrealistic enrollment rates often lead to inaccurate predictions of when the clinical trial will be completed. Accordingly, some embodiments include incorporating more realistic enrollment rates based on historical data, past performance and/or statistics on enrollment rates for similar types of trials.

As discussed above, unrealistic enrollment rates may also result from the assumption that all sites begin enrolling at substantially the same time. However, as discussed above, there may be substantial variation in when sites in different countries begin enrolling patients. By modeling a more realistic enrollment rate and enrollment delay (see e.g., information 320 and 328 in FIG. 3, respectively), patient recruitment may be better predicted. Timeline 630 was generated using the factors incorporated into the model for timeline 620, plus additionally incorporating the more realistic enrollment properties. Accordingly, by modeling a number of factors identified by Applicant as impacting patient recruitment, a patient recruitment timeline may be generated that may closely align with the timeline of the actual clinical trial, as shown by the similarity of timelines 630 and 640.

When planning a clinical trial, the sponsor of the clinical trial may want to have the clinical trial performed in the shortest amount of time, while adhering to budgeted financial and time resources. Decisions regarding the number of countries and the number of sites within each country impacts this cost/duration balance. Applicant has appreciated that some combination of factors described in the foregoing may be used to assist a sponsor in quickly ascertaining whether a planned clinical trial will achieve the cost/duration goals of the sponsor. The software tool, of which a screen of a portion is illustrated in FIG. 3, may additionally include one or more features that facilitate relatively quick assessment of whether a clinical trial being planned is consistent with the sponsor's goals, and/or may include one or more features that allow the clinical trial to be modified or customized with relative ease to reach a clinical trial timeline that is consistent with the sponsor's goals.

According to some embodiments, information table 300 may further comprise entries for recruitment goals 350, timeline goal information 360, and indicator information 370 to allow a clinical trial designer (e.g., the sponsor) to enter high level information about the expectations of the clinical trial. Recruitment goals 350 may include entries for a targeted number of sites for the clinical trial and a targeted number of patients to screen and/or enroll. Recruitment goals information may include other entries for entering information related to patient recruitment goals that may be used to measure whether a clinical trial is on track or otherwise proceeding substantially as planned. A sponsor may also enter timeline goal information 360, for example, initiation start information (the estimated time when the first site is initiated), end of enrollment information (the estimated time when the last patient is enrolled), end of clinical trial information (the estimated time when the last patient in the clinical trial will complete all patient visits), or other entries related to goals for the length of the trial with respect to the selected sites.

Recruitment goals 350 and timeline goal information 360 may be linked to other information in information table 300 to assist in clinical trial planning. For example, recruitment goals 350 and timeline goal information 360 may be linked to enrollment duration information 330, and recruitment table 500 illustrated in the screen shot of the recruitment portion of the software tool (see FIG. 5). Differences between the estimated patient recruitment timeline shown in recruitment table 500 and the targeted information indicated in recruitment goals 350 may be displayed as indicator information 370. That is, indicator information may provide information related to the extent to which the clinical trial goals are or are not being met by the current information entered into the tool.

Indicator information 370 may include text information indicating the numerical difference between the predicted information in recruitment table 500 and the recruitment goals 350. Alternatively, indicator information 370 may employ color-coded information, or any other suitable indication of whether the model built on predictive factors is aligned with the goals of the clinical trial, and in some cases, may indicate the extent of the departure from the goal information entered into the software tool.

For example, if recruitment goals 550 indicates that five hundred patients were targeted to be screened, and the predicted value is within −5% to +20% of the targeted value, a green indication may be used indicating that the predicted value is within reasonable limits necessary to achieve the goals of the clinical trial. However, if the predicted value is outside of these limits, an alert level color may be used instead of green. For example, if the predicted value is 5% to 15% below the targeted value, a yellow alert may be used to indicate that minor modifications to the clinical trial strategic plan may be necessary. If the predicted value is more than 15% below the targeted value, a red alert may be used to indicate that major modifications to the strategic plan may need to be implemented if the goals are to be achieved.

Further, if the predicted value is more than 20% above the targeted value, a blue alert may be used to indicate that some aspects of the clinical trial plan may be too aggressive (e.g., some sites may be unnecessary) and the cost may be reduce by removing unnecessary sites while still reaching the goals set forth in the software tool. In one implementation, the thresholds for various alert colors may be user-configurable, and the ranges above are provided merely for illustrative purposes. It should be appreciated that any number of alert colors and/or ranges may be used to implement indicator information 370, as the aspects of the invention are not limited for use with any particular type of indicator.

In addition to providing display indications, classifying sites based on their actual performance relative to predicted performance or goals may be used for other data processing operations. Such classifications can be used, for example, to select groups of sites for further data processing operations. For example, a group of underperforming sites may be selected and processed to identify one or more underperforming sites that may be dropped from the clinical trial. Such an adjustment to the clinical trial plan may be automated or may be based on displaying a group of sites selected based on an assigned classification. Though, any other suitable data processing operation may be performed based on performance classifications.

Accordingly, the prediction and goal information may facilitate planning a better, more efficient and/or more cost effective clinical trial. For example, manipulation of recruitment goals 350 and/or timeline goal information 360 in combination with other information in information table 300 allows for a sponsor to set up and observe various "what if" scenarios to see how the model reacts to changes in various recruitment parameters. For example, a sponsor may set goals of having one-hundred sites, screening five-hundred patients, enrolling two-hundred and fifty of the five-hundred screened patients, and having a clinical trial duration of one year. After generating a patient recruitment timeline for the clinical trial using some combination of the factors described herein, indicator information 370 may indicate that the predicted timeline generated from the information in information table 300 predicts that only four-hundred patients are likely to be screened during the proposed one year time period.

Thus, to achieve the goals for the clinical trial, the parameters of the clinical trial may be modified and the results observed in real time. Alternatively, a sponsor may compromise and make one or more goals (e.g., patient recruitment goals, completion date, etc.) less aggressive. For example, the total number of sites may be increased, the targeted number of patients to be screened can be lowered, the length of the clinical trial can be extended, and/or the type of sites (e.g., simple vs. complex, where the sites are located, etc.) may be changed. By making adjustments to various parameters in information table 300 and/or setting more modest goals prior to beginning a clinical trial, a sponsor of a clinical trial may be provided with realistic expectations as to the cost, length, and resources involved in the clinical trial, and can make the necessary adjustments at the outset of the clinical trial.

Applicant has appreciated that another tool that may facilitate management of a clinical trial includes a tool that maintains and manages information to facilitate data and resource management during a clinical trial, and not just during the planning phase of a clinical trial. In some embodiments, predicted and actual recruitment information may be tracked as patients are screened and/or enrolled in the clinical trial at various sites to monitor how well sites are keeping up with the predicted timelines. By comparing actual recruitment data with the predicted timelines, an assessment of how the clinical trial is progressing may be obtained. In addition, projections as to how long a clinical trial will take to complete based on data about the current status of the clinical trial may be computed by projecting the current data into the future. Thus, predicted timelines may be used to assess how well a clinical trial is progressing and projecting when the clinical trial will likely be completed based on the current status of patient recruitment. Tracking and monitoring of a clinical trial may facilitate identifying problems in patient recruitment early on and/or assist in identifying problematic sites (or over-performing sites) so that remedial measure may be taken.

Figure 7:
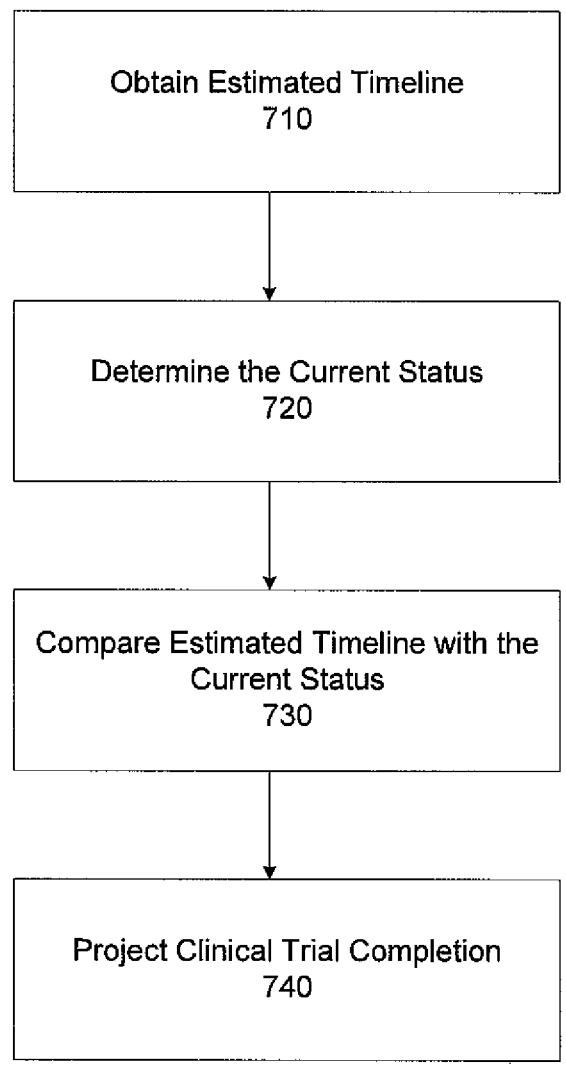
FIG. 7 is a flowchart of a process for tracking a current status of a clinical trial.

FIG. 7 illustrates a method for assessing a current state of a clinical trial and projecting, based on the current state, an estimate for when the clinical trial will be complete, in accordance with some embodiments of the present invention. In act 710, an estimated recruitment timeline is generated and obtained. For example, an estimated recruitment timeline may be obtained using any one or combination of methods described above, such as incorporating one or more factors that tend to cause patient recruitment timelines to depart from straight-line extrapolation models into a model for patient recruitment. A predicted timeline may be generated for the entire clinical trial, individual countries and/or specific sites, as the aspects of the invention are not limited in this respect.

In act 720, after at least some actual data related to patient recruitment has been obtained, the status of the clinical trial at a given moment in time is determined. For example, at some point in the patient recruitment process, data related to the number of patients screened and/or enrolled may be obtained from the various sites in the countries selected to participate in the clinical study. This data may be used as a baseline to indicate the status of the clinical trial. The status indicator may be, for example, the total number of patients screened and/or enrolled at the time the data was obtained. The status indicator may be more complex to incorporate further information, as discussed in further detail below. It should be appreciated that determining the status of the clinical trial may be performed at any time and/or multiple times throughout the clinical trial to assess the current state of the clinical trial at any desired moment in time. In addition, status indicators may be generated for the entire clinical trial, for the individual countries participating in the trial and/or for specific sites, as the aspects of the invention are not limited in this respect.

In act 730, the status indicator is compared to the estimated timeline at the corresponding moment in time to estimate the extent, if any, of any deviation of the actual data from the estimated patient recruitment timeline (either as exceeding or failing to meet expectations). For example, if the status indicator includes the total number of patients enrolled by a given date, this number may be compared to the estimated timeline for enrolled patients at the same date. Similarly, if the status indicator includes the total number of patients enrolled by a given date in individual countries, this number may be compared to estimated timelines generated on a per country basis. The result of the one or more comparisons provide an indication of how well the clinical trial is proceeding with respect to the one or more estimated timelines to provide an assessment as to the current state of the clinical trial. As a result, the state of the clinical trial may be monitored throughout, such that any issues may be addressed, as discussed in further detail below.

In some embodiments, the current status is used as a baseline to project when the clinical trial will be completed based on the actual recruitment data obtained on a given date. In act 740, a projection method is applied to the current status information to project the date at which the goal number of patients will be screened and/or enrolled. The projection method may be a straight-line extrapolation from the current state, or may incorporate previous month trends to project when patient enrollment will be complete.

In some embodiments, an enrollment rate from a prior interval, such as the preceding month, may be increased based on new sites that began enrolling or are projected to begin enrolling patients after that prior interval. Conversely, if sites have stopped enrolling, or are projected to stop enrolling patients, after that prior interval, the enrollment rate to be used in making the projection may be decreased. The adjusted enrollment rate may then be used to project enrollment.

Any projection method may be used, and the projection method may be user-selectable, as discussed in further detail below. Such projected timelines may be formed for the entire clinical trial, the individual countries and/or specific sites participating in the clinical trial. Moreover, such projections may be used to determine values other than a study completion time. Such a projection, for example, may be used to determine an enrollment timeline for any other purpose, including to schedule monitoring visits a one or more clinical trial sites.

FIG. 8 illustrates a screen shot of a portion of a software tool designed to facilitate management during a clinical trial. In particular, the software tool includes features that facilitate determining the status of a clinical trial and/or projecting, based on the current status, when the clinical trial will be completed. The software tool may be part of or separate from other software tools described herein. In FIG. 8, actual recruitment data may be entered in recruitment management summary 800 to facilitate tracking the progress of a clinical trial. The recruitment data for a site may be entered in recruitment management summary 800 by a CRA who monitors the site, or by any other qualified individual in possession of the appropriate data. The data may be manually entered by the CRA or the data may be automatically entered using voice recognition algorithms or other automatic data entry methods.

According to some embodiments, recruitment management summary 800 may include a table comprising a plurality of sections in which data for each site in a clinical trial may be entered. In FIG. 8, the recruitment management summary 800 may include site identification information having entries for country information 802, site number information 806, site name information 808, and CRA information 810. The CRA information may indicate the CRA that has been assigned to monitor the site, or any person who is responsible for collecting and reporting recruitment information 820 over the course of the clinical trial.

Recruitment information 820 may comprise expected recruitment information 822 and actual recruitment information 824 corresponding to data related to the expected number of patients to be screened and enrolled, and the actual number of patients screened and enrolled, as observed and collected during the performance of the clinical trial, respectively. Expected recruitment information 822, for example, may be generated based at least in part on information entered in information table 300 such that one or more estimated timelines may be generated using one or more estimation methods described herein, either for the entire clinical trial, individual countries and/or individual sites. Thus, the one or more estimated timelines may be used to determine how well a clinical trial is progressing with respect to the timeline predicted at the outset.

As discussed above, during the clinical trial, a CRA assigned to monitor a site may periodically visit the site for various reasons. For example the CRA may wish to verify that the site is following the established procedures, answer any questions that researchers at the site may have concerning the clinical trial, collect current recruitment information including the number of patients screened and the number of patients enrolled, collect completed case report forms (CRFs), etc. The actual number of patients screened and/or enrolled in the clinical trial at each site may then be entered by the CRA assigned to the site or any other individual to generate and archive actual recruitment information 824 in the recruitment management summary 800.

It should be appreciated that actual recruitment information 824 may be collected in any suitable way, and the aforementioned method of collecting actual recruitment information 824 by a CRA during a monitoring visit is merely provided as an example of how actual data may be obtained. For example, actual recruitment information 824 may be transmitted from research personnel at a clinical trial site to a CRA or other qualified individual via telephone, mail, facsimile, electronic mail, web-based application, or by any other suitable means, as the aspects of the invention are not limited for use with any particular method of obtaining or otherwise gathering actual clinical trial data.

Pursuant to entering at least some actual recruitment information 824 in recruitment management summary 800, the expected recruitment information 822 and the actual recruitment information 824 may be compared to assess the state of the clinical trial. For example, the comparison may include calculating the total number of patients screened and/or enrolled and the average rate (e.g., number of patients/month) at which patients are being enrolled at each site. This information may be represented as total patient information 830 and rate information 840, respectively, in recruitment management summary 800. The deviation of the actual recruitment information 824 from the expected recruitment information 822 for each site may be indicated as recruitment status indicator 804. In some embodiments, recruitment status indicator 804 may include text information indicating a numerical difference between the expected recruitment information 822 and the actual recruitment information 824, or may include other types of indicators to indicate the current status of the clinical trial.

This information may allow individuals monitoring a clinical trial to quickly identify the recruitment performance of sites relative to expectations. For example, an assessment of site recruitment performance may be used to determine if certain sites should be discontinued (if they are underperforming), if a CRA should be sent to visit certain sites if they are over performing (because they may have accumulated many CRFs), or to make any other management decisions regarding the clinical trial. Thus, to indicate site performance, recruitment status indicator 804 may include text information, color-coded information, or any other suitable indication of the degree to which recruitment at the site is meeting expectations.

In one example, if the number of patients actually enrolled at a site is within −5% to +20% of the expected number of enrolled patients, a green indication may be used to quickly identify that the site has enrolled an acceptable number of patients relative to expectations. However, if the actual number of patients enrolled is outside of these limits, a color other than green may be used. For example, if the actual number of enrolled patients is 5% to 15% below the expected value, a yellow indicator may be used to indicate a site may be lagging in recruitment performance. If the actual number is more than 15% below the expected value, a red indicator may be used to indicate an at risk site that may have one or more issues that need to be addressed.

By contrast, if the actual number is more than 20% above the expected value, a blue indicator may be used to indicate a site is performing better than expected. The color status may facilitate efficiency in identifying and correcting sites that are underperforming, and identifying sites that are over performing to, for example, shift some burden to over performing sites, close down at risk sites, obtain information regarding why particular sites are performing well (or poorly), and/or otherwise reconfigure the clinical trial to help maintain the desired timeline.

The thresholds for the different colors may be user-configurable to allow a sponsor or individuals managing a clinical trial to customize the indicators to best suit a particular clinical trial. It should be appreciated that the ranges above are provided merely for illustrative purposes, and that any number of color indicators, numerical indicators, ranges, and/or any other indicators may be used with recruitment status indicator 504 to indicate trial status, as aspects of the invention are not limited in this respect.

The current status of the clinical trial may be used to project when the clinical trial will be complete and/or to project when a particular country or site will complete its portion of the clinical trial (e.g., to project when the last enrolled patient completes the final visit). The projected timeline from the current status may be projected using any number of methods. For example, a straight line extrapolation from the current data may be performed, or the projection method may incorporate recruitment data from the previous month to project how the sites will perform in the upcoming months. The projection method may be selectable so that a user may select the projection method from a list of possible projection methods by, for example, entering the name of the preferred projection method in a field in recruitment management summary 800 or by indicating the preferred projection method in any other suitable way, such as by selecting the preferred projection method from a drop-down menu.

Figure 9:
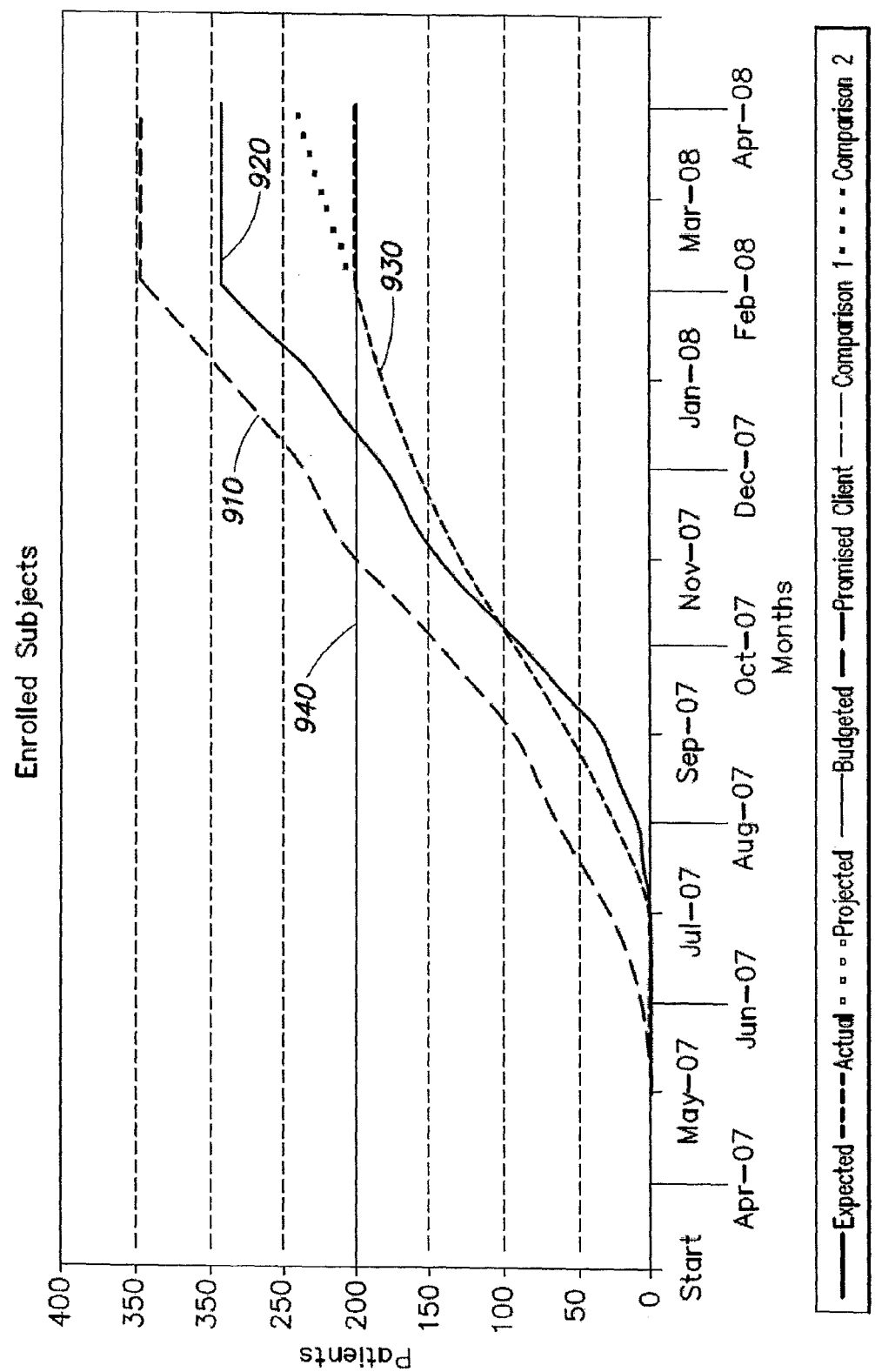
FIG. 9 is a sketch of output produced by a tool clinical trial planning and management showing an idealized timeline, an estimated timeline and a projected timeline based on actual recruitment data.

To assist in assessing the current state of a clinical trial, the software tool may include features that allow one or more reports which graphically illustrate patient recruitment timelines for each site, for each country, and/or for the entire clinical trial. FIG. 9 shows an enrollment timeline 900, which compares an ideal time, an estimated timeline and a projected timeline based on actual recruitment data to visualize how a clinical trial is proceeding.

In the example of FIG. 9, line 910 is a recruitment timeline that was initially desired by the sponsor, line 920 is an expected recruitment timeline based on, for example, information provided in information table 300, and line 930 is the actual recruitment timeline calculated after actual clinical trial data has been obtained from one or more sites participating in the trial. Patient recruitment 940 illustrates the total number of patients enrolled at the time the actual recruitment data was obtained from the sites participating in the study. The actual data obtained from the various sites during the clinical trial are shown as a function of time as the solid portion of timeline 930. Based on this information, a straight-line extrapolation may be performed to project, based on the current status, how the clinical trial will perform in the upcoming months to visualize when the clinical trial will complete based on the current status. Such projections allow a sponsor or a company assisting in managing trials take measures to re-allocate resources or otherwise enact remedial measures to make sure a clinical trial stays on track.

Figure 10:
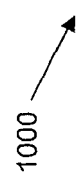
FIG. 10 is a sketch of an output format for a tool generating clinical trial planning and management data.

In some embodiments, a software tool for clinical trial management may include features that allow the data (e.g., the data entered in recruitment management summary 800) to be visualized in other ways. For example, the number of patients actually screened and/or enrolled in the clinical trial compared to recruitment expectations may be indicated for each country as shown the country summary illustrated in FIG. 10. Each country may have an associated indicator to indicate the recruitment performance of the country relative to expected recruitment levels. Alternatively, country reports may be graphically presented in the form of charts and/or graphs.

Figure 11:
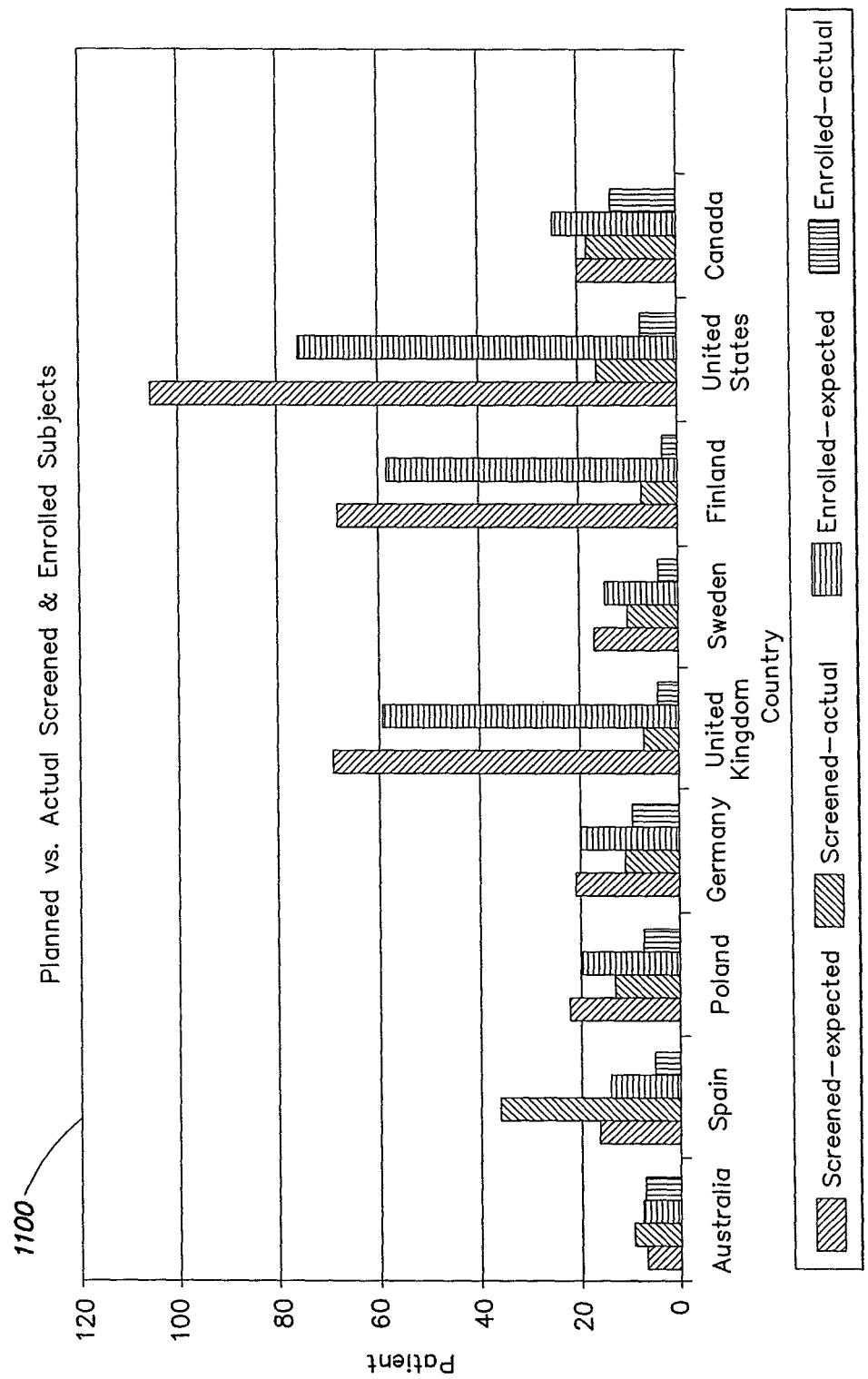
FIG. 11 is a sketch of an alternative output format for information generated by a tool for clinical trial planning and management.

FIG. 11 illustrates a bar graph 1100 for comparing the recruitment performance of sites in various countries participating in a clinical trial. As shown in the example of FIG. 11, Spain has screened more than the expected number of patients, yet has enrolled fewer patients than expected. In contrast, other countries such as the United States have both screened and enrolled fewer patients than expected. Other forms of visualization may also be used to assist in monitoring and/or managing a clinical trial and may be useful tools to alert clinical trial management personnel about imbalances in country or global recruitment, such that management decisions may be made to, for example, close down certain sites and/or to redirect resources to sites/countries/global regions as deemed appropriate.

Applicant has appreciated that a substantial bottleneck in clinical trials may often be human resource allocation, and more particularly, CRA resource allocation and management. Thus, Applicant has developed a data management facility which may assist in estimating human resource allocation, including timelines of when CRAs should be available to visit sites participating in a clinical trial. When a CRA should visit a site during a clinical trial may vary from site to site, and may depend on one or more factors related to the progress of the individual sites. For example, whereas a CRA may need to visit each site to which they are assigned in order for the site to go live (i.e., when the site may begin screening and enrolling patients), the next time the CRA may need to return to the site for a monitoring visit may be based on the recruitment performance of the site. That is, whereas the CRA may primarily provide training for research personnel and ensure that the site has met all regulatory measures during an initial monitoring visit, subsequent monitoring visits may primarily be focused on data collection and evaluation of a site's compliance with procedure and protocol.

As discussed above, data for each patient in a clinical trial may be recorded by research personnel at each site on clinical research forms (CRFs) or other standardized forms to ensure consistent data entry for all patients in the clinical trial. During the enrollment period in a clinical trial, a patient may be required to have a series of patient visits during which the performance and/or health of the patient are evaluated by a doctor or other clinical research professional. The data recorded during such patient visits may be recorded on a CRF, or a similar type of standardized form. In addition to data recorded on CRFs, patients screened and/or enrolled in the clinical trial may be asked to periodically fill out one or more questionnaires, such as a quality of life (QOL) questionnaire and/or to write entries in a diary to document various aspects of their health performance during the course of the clinical trial. A substantial portion of a CRA's monitoring visit to a site may be to collect and/or verify the data recorded using these various methods (e.g., QOL and diary, CRF, etc.) for each patient currently screened and/or enrolled at the site. Thus, a determination of when a CRA should schedule a monitoring visit may be at least partially dependent on the amount of data to be collected at a site.

Additionally, a sponsor may wish to periodically have updated outcome projections (e.g., to facilitate managing and identifying problems in the clinical trial) based on the data collected thus far in the clinical trial. To accomplish this, data should be collected from each site within a reasonable time frame such that any outcome projections that are made based on the data collected accurately reflect the state of the data when the outcome projections are made to avoid making projections on stale data. Thus, it may also be important to schedule CRA monitoring visits using a predetermined time period, such that data is collected regularly and in a timely manner for all of the sites in the clinical trial.

FIG. 12 illustrates monitoring information 1200 that may be used to manage CRA resources. For example, monitoring information 1200 may include one or more factors to project when CRAs should be made available to schedule monitoring visits at the sites participating in the clinical trial. Some factors may include the time spent reviewing a CRF page and/or a QOL or diary page, the additional time a CRA may spend at a site (e.g., time spent discussing matters with research staff, accounting for used pharmaceuticals, etc.), and the total time the CRA is estimated to be at a site (i.e., total time on site). The amount of time that is indicated as the total time on site may be used to establish a threshold, which when exceeded, provides an indication that a CRA should schedule a monitoring visit for the site. Monitoring information 900 may further comprise monitoring frequency information indicating a predetermined amount of time that may pass between scheduled monitoring visits.

In some embodiments, one or more monitoring methods may be used to generate one or more CRA monitoring visit timelines based at least in part on the monitoring information 1200. For example, scheduling of monitoring visits may be determined primarily on the number of data pages (e.g., CRFs and QOL/diary pages) to be collected at a site, without deference to a maximum amount of time between the visits. Alternatively, scheduling of monitoring visits may be based primarily on predetermined timing of visits, rather than on the number of data pages to be collected at a site. Yet another monitoring method may include a hybrid of the two aforementioned methods by taking into consideration the number of data pages to be collected at a site and a maximum time between site visits. For example, a hybrid method may establish a threshold for each consideration, and when at least one of the thresholds is exceeded, an indication to schedule a monitoring visit for a site may be provided.

In some embodiments, an estimate of the expected number of monitoring site visits for each site in the clinical trial may be determined based at least in part on monitoring information 1200 and at least some site-dependent information, such as information provided in recruitment management summary 800. For example, the expected number of data pages (e.g., CRF and QOL/diary pages) available to be collected at a site and the expected number of monitoring site visits during predetermined periods of time (e.g., visits/month) may be displayed as CRA visit information 1300 (see FIG. 13). As shown in FIG. 13, site 101 in Australia is expected to have a total of 826 CRF pages to be collected over the duration of the clinical trial. This number may be determined, for example, by multiplying the expected number of patients to be screened/enrolled at the site by a predetermined number of CRF pages that must be collected for a patient who has completed all of the patient visits. Alternatively, the expected total number of CRF pages for a site may be determined by adding the expected number of CRF pages determined for each month of the clinical trial.

In some instances, the expected number of CRF pages for each month at a site may be based at least in part on a patient recruitment timeline estimated using information in information table 300, and/or using information provided in recruitment management summary 800. For example, a patient recruitment timeline estimated for sites in Australia may indicate that the patient screening expectation for each site is five patients per month during the first two months of the clinical trial, three patients per month during the next two months, and two patients per month for the remainder of the clinical trial. If the screening period for the clinical trial is one month, and ten CRF pages are collected for a patient who has completed screening, it may be estimated that fifty screening CRF pages (5 patients×10 CRFs) will be available for collection at month two, fifty CRF pages at month three, thirty CRF pages (3 patients×10 CRFs) at month four, etc. In some embodiments, the expected number of CRF pages at a site may be adaptively updated as the clinical trial progresses so that the estimated number of CRF pages in future months is based at least in part on the recruitment performance of the site during prior months of the clinical trial.

CRA visit information 1300 may further comprise expected monitoring visit information which may be calculated based, at least in part, on the expected number of CRFs indicated in CRA visit information 1300 and/or monitoring information 1200 depending on the monitoring method that is selected. For example, if the selected monitoring method is a hybrid method, at least two factors may contribute to the determination that a CRA monitoring visit should be scheduled. A first factor may establish a threshold based on the expected number of data pages (e.g., CRFs and QOL/diary pages) at a site, and a second factor may establish a threshold based on a maximum time elapsing between visits. Together these two factors may determine an expected CRA monitoring visit schedule for each site, such that the number of CRAs that will be required for site visits during each month (or some other predetermined time period) during the clinical trial may be estimated prior to beginning the clinical trial, and may be maintained throughout the course of the trial.

Applicant has further that the expected number of CRF's and/or QOL/diary pages available for collection may be impacted by patient retention. Clinical trials are typically subject to at least some patient attrition, that is, at least some patients typically quit the trial before completion due to the hardships of the trial or for personal reasons. Thus, computing the expected amount of data to be collected each month without considering patient attrition may result in inflated estimates of how much data will be available for collection in a given month, resulting in inefficient use of CRA resources. Accordingly, in some embodiments, patient retention rates are modeled to better predict the amount of data that will be available at the various sites participating in the clinical trial, for example, on a month-to-month basis.

FIG. 14 illustrates a screen shot of a tool that may be used to incorporate patient retention into the model for computing the expected amount of data to be available for collection each month. In particular, patient document completion schedule 1400 includes entries 1410 for indicating the expected patient retention for each month of the clinical trial. Entries 1420 and 1430 show the results of the data expected to be available for collection after patient retention has been factored in. The amount of data (e.g., CRF's, QOL/Diary pages, etc.) expected to be available each month may be input into entries 1420 and 1430 after it has been determined using any of the methods described in the foregoing, or it may be linked to other tables that store this information. The expected amount of data may then be multiplied by the retention rate to generate the amount of data expected for each month, reduced by the predicted levels of patient attrition.

Patient attrition may be determined from historical data on particular types of trials, past attrition rates in particular countries, or using any other suitable method. For example, in the exemplary trial for which patient retention rates are illustrated in FIG. 14, it may be known from experience that this particular type of trial has difficult patient visits and requirements in months three and five of the trial (e.g., historical data shows that may patients quit the trial for this particular type of trial during these months). Accordingly, the patient retention percentages may be reduced for those months to account for the fact that a higher percentage of patients are expected to leave during these months, resulting in less data available for collection. Accordingly, patient retention may be incorporated into the model for estimating the amount of data available for collection each month at the various sites participating in the clinical trial. Patient retention estimates may be determined based on any information deemed reflective of patient attrition, as the aspects of the invention are not limited in this respect.

In some embodiments, reports may be generated, based on the information provided in CRA visit information 1300. For example, a numerical report may be generated in which the number of expected CRA visits for each country is shown as country CRA visit information 1500, as illustrated in FIG. 15. By determining the number of CRA visits in each country, those responsible for monitoring the clinical trial may be better able to predict when each country may need to staff CRAs to perform the expected number of monitoring visits. Such an assessment may allow for a better allocation of human resources (e.g., CRAs) by having enough CRAs available to perform monitoring visits at certain times during the clinical trial when visits are expected to be most needed, while avoiding situations where there is CRA availability but no data to collect. Thus, providing a more accurate determination of CRA monitoring visit timelines may help prevent delays in collecting data in a timely manner, and avoid stranding CRA resources.

Figure 16:
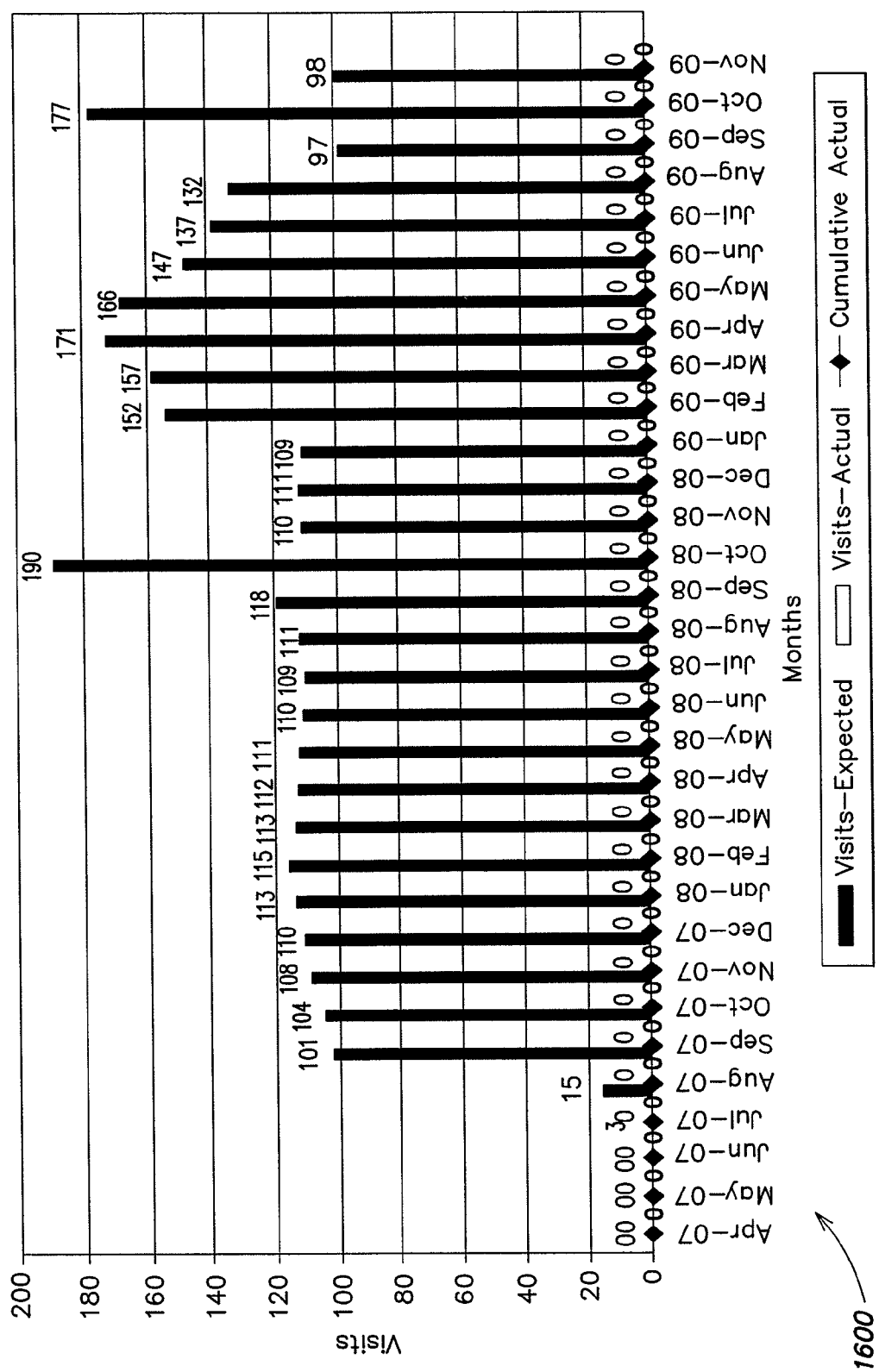
FIG. 16 is a sketch of an alternative format for presenting information relating to monitoring visits.

Other reports including, but not limited to, graphical reports such as CRA distribution plot 1600 shown in FIG. 16 may also be generated based on information provided in CRA visit information 1300. CRA distribution plot 1500 illustrates a total expected number of monitoring visits for each month of a clinical trial. For example, in the example of FIG. 13, it has been estimated that 190 monitoring visits will be required in October, 2008, which is substantially more visits than expected for the months surrounding October, 2008. By being aware of the number of CRAs expected to perform monitoring site visits in each month of a clinical trial, management companies who employ the CRAs may be better informed to staff the appropriate number of CRAs at particular times of the year to reduce delays that may occur because of a lack of available CRAs at any given time.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A tool for clinical trial management, the tool comprising:
computer storage media encoded with data defining:
factors affecting patient enrollment rates during a clinical trial, the factors defining:
non-uniform rates of patient enrollment in different time intervals of a plurality of time intervals at each of a plurality of clinical trial sites; and
different rates of patient enrollment in different clinical trial sites of the plurality of clinical trial sites during the same time interval of the plurality of time intervals; and
computer storage media encoded with computer executable instructions for, when executed on a processor:
computing a patient enrollment timeline for the clinical trial, the computing comprising, using the factors, including the factors defining non-uniform rates of patient enrollment, projecting a number of patients enrolled at the plurality of sites during each of the plurality of time intervals; and
providing as an output the patient enrollment time line.

2. The tool of claim 1, in combination with components of a computer system, wherein the components of the computer system comprise:
a display device;
an input device; and
computer executable instructions for displaying on the display device at least a portion of the factors and receiving user input through the input device specifying modifications to the factors, whereby the patient enrollment timeline output by the computer system is computed using the modified data defining non-uniform patient enrollment rates.

3. The tool of claim 1, wherein:
the data identifies countries in which the plurality of clinical trial sites are located; and
the computing comprises, based on the factors, computing for each of the plurality of intervals, a number of clinical trial sites starting enrollment in each country of the identified countries.

4. The tool of claim 3, wherein:
computing the number of clinical trial sites starting enrollment comprises, for each identified country, a base date plus a regulatory delay factor representing regulatory delay in the country.

5. The tool of claim 1, wherein:
the data identifies countries in which the plurality of clinical trial sites are located;
the factors affecting patient enrollment rates comprise a fraction of a nominal enrollment rate applicable in each of the countries in each of a plurality of calendar intervals, the fraction being based at least in part on holidays in the country; and
the computing comprises, for each study interval of the plurality of intervals:
associating a calendar interval with the study interval;
selecting, based on the calendar interval, a fraction for each country of a plurality of countries in which clinical trial sites exist; and
computing a number of patients enrolled based on the nominal rate for each of the plurality of sites scaled by the selected fraction applicable to the county in which the site is located.

6. The tool of claim 1, wherein:
the factors comprise:
a delay factor defining a delay between patient screening and patient enrollment; and
an enrollment factor defining a percentage of patients screened that are enrolled; and
the computing comprises:
projecting a number of patients screened in each of a plurality of intervals; and
calculating a number of patients enrolled in each of a plurality of intervals based on a number of patients screened in a prior interval of the plurality of intervals scaled by the enrollment factor, the prior interval being selected based on the delay factor.

7. The tool of claim 1, further comprising:
computer storage media encoded with computer executable instructions for, when executed on a processor:
comparing the computed patient enrollment timeline to recruitment goals for the clinical trial; and
rendering an output on a display device indicating deviations between the recruitment goals and the computed patient enrollment timeline.

8. A non-transitory computer storage medium encoded with computer executable instructions that, when executed by a computer, control the computer to perform a method comprising:

computing, for each of a plurality of time intervals, a projection of a number of patients enrolled in a clinical trial, the computing comprising:

obtaining data identifying a plurality of clinical trial sites;

obtaining data defining non-linear patient enrollment rates at each of the plurality of clinical trial sites; and computing, using the data defining non-linear patient enrollment rates, a projected number of patients enrolled for each of the plurality of sites during each of the plurality of time intervals.

9. The computer storage medium of claim 8, wherein:

the data identifying a plurality of clinical trial sites comprises data identifying a geographic location of each of the plurality of clinical trial sites; and obtaining data defining non-linear patient enrollment rates at each of the plurality of sites comprises obtaining data defining non-linear patient enrollment rates in the geographic location of each of the plurality of clinical trial sites.

10. The computer storage medium of claim 8, wherein:

the computer storage media further comprises a data store containing data indicating a reduction factor for each of a plurality of geographic locations; and obtaining data defining patient enrollment rates comprises computing, for each of a plurality of geographic locations, an enrollment rate based on the reduction factor.

11. The computer storage medium of claim 10, wherein:

the data store further comprises data indicating a projected delay between study initiation and first patient enrollment in each of the plurality of geographic regions; and computing a projected number of patients enrolled comprises, for each of the plurality of sites:

obtaining data defining the study initiation date for the trial site;

accessing the data store to determine the projected delay for the geographic region for the trial site;

computing an initiation point based on the study initiation date and the projected delay; and computing, using the data indicating patient enrollment rates accessed in the data store, patient enrollment subsequent to the computed initiation point.

12. The computer storage medium of claim 11, wherein: the method further comprises:

rendering on a display a user interface presenting the data from the data store indicating patient enrollment rates as default values;

accepting user input altering a default value presented in the user interface;

selectively employing default values and user input to compute the projected number of patients enrolled, the selectively employing comprising:

when user input altering a default value is received, using the altered value during the computing of the projected number of patients enrolled during each of the plurality of time intervals; and when no user input altering a default value is received, using the default value during the computing of the projected number of patients enrolled during each of the plurality of time intervals.

13. The computer storage medium of claim 8, wherein:

the data defining non-linear patient enrollment rates comprises, for each of a plurality of countries, an indication of a percentage of sites starting patient enrollment in each of a plurality of time intervals; and the computing the projected number of patients enrolled is based in part on the indication of the percentage of sites starting patient enrollment in each of a plurality of time intervals.

14. The computer storage medium of claim 13, wherein:

the plurality of sites comprises a number of sites classified as simple sites and a number of sites classified as complex sites; and for each of the plurality of countries, a first percentage is associated with simple sites and a second percentage, different than the first percentage, is associated with the complex sites; and for each of the plurality of countries, the computing based in part on the indication of the percentage of sites comprises computing a number of sites starting patient enrollment based on the first percentage multiplied by the number of simple sites and the second percentage multiplied by the number of complex sites.

15. The computer storage medium of claim 14, wherein the first percentage and the second percentage are obtained based on historical data.

16. The computer storage medium of claim 8, wherein the method further comprises:

controlling an output device to render a report indicating aggregate enrollment in the clinical trial during each of the plurality of time intervals.

17. The computer storage medium of claim 8, wherein the method further comprises:

for each of at least a portion of the plurality of clinical trial sites, comparing a number of patients enrolled to a recruitment goal for the clinical trial site; and classifying each of the at least a portion of the plurality of sites based on the comparison between the number of patients enrolled and the recruitment goal.

18. The computer storage medium of claim 17, wherein the method further comprises:

displaying information relating to the at least a portion of the plurality of clinical trial sites with a tag identifying the classification of the clinical trial site.

19. The computer storage medium of claim 17, wherein the method further comprises:

selecting for a data processing operation a subset of the plurality of clinical trial sites having the same classification.

20. A method of operating a computer to produce an enrollment timeline for a clinical trial, the method comprising:

computing, using a processor of the computer, a recruitment timeline, the computing comprising:

obtaining data identifying a plurality of clinical trial sites, said data including, for each clinical trial site, a country in which the clinical trial site is located;

obtaining data defining a plurality of factors relating to patient enrollment rates at each of the plurality of clinical trial sites, the factors comprising a country-dependent factor and a site-dependent factor;

computing, using the plurality of factors, including the factors relating to patient enrollment rates, a projection of a number of patients enrolled for each of the plurality of sites during each of a plurality of time intervals; and outputting, as the clinical trial enrollment timeline, a projection of a number of patients enrolled in a clinical trial for each of a plurality of time intervals.

21. The method of claim 20, wherein the plurality of factors further comprise a site fatigue factor that specifies a decrease in a patient enrollment over time.

22. The method of claim 21, wherein the plurality of factors comprises a set of values representing a fraction of a nominal rate applicable in each of the plurality of time intervals, and the site fatigue factor is represented by a decrease in the fraction in later time intervals of the plurality of intervals.

23. The method of claim 20, wherein:
the plurality of site-dependent factors comprises a database factor indicating a clinical trial site of the plurality of clinical trial sites having a database of potential patients; and
the computing comprises, based on the database factor, increasing the rate of patient enrollment during an initial portion of the plurality of time intervals for the clinical trial site having the database.

24. The method of claim 20, wherein:
the plurality of site-dependent factors comprises a complexity factor having a value indicating whether a clinical trial site that is a more complex organization or a less complex organization; and
the computing comprises, based on the complexity factor, determining a number of sites enrolling patients during an initial portion of the plurality of time intervals, the determined number comprising a lower percentage of sites that are more complex organizations than are less complex organizations.

25. The method of claim 20, further comprising:
obtaining data indicating actual patient enrollment at each of the plurality of sites;
comparing the actual enrollment to the projection of a number of patients enrolled to identify sites of the plurality of sites that are behind the projected enrollment; and
producing an output indicating the identified sites.

26. The method of claim 20, further comprising:
obtaining data indicating actual patient enrollment at each of the plurality of sites;
modifying the projected enrollment based on the actual patient enrollment; and
producing an output indicating projected clinical trial study completion date based on the modified projected enrollment.

27. The method of claim 20, wherein obtaining data defining a plurality of factors relating to patient enrollment comprises analyzing historical data to compute the factors.

28. The method of claim 20, wherein the method further comprises:
obtaining data indicating actual patient enrollment at a time;
computing, based on the actual patient enrollment, an enrollment rate;
computing, based on a projected change in the number of clinical trial sites enrolling patients subsequent to the time, an adjusted enrollment rate; and
for a plurality of time intervals subsequent to the time, computing a projection of the number of patients enrolled in the clinical trial based at least in part on the adjusted enrollment rate.

* * * * *